(12) United States Patent
Feng et al.

(10) Patent No.: US 7,067,472 B1
(45) Date of Patent: Jun. 27, 2006

(54) DIAGNOSTIC AND THERAPEUTIC METHODS RELATED TO REGULATING ENERGY MOBILIZATION WITH OB PROTEIN AND OB ANTIBODIES

(75) Inventors: Lili Feng, San Diego, CA (US); Shizhong Chen, San Diego, CA (US); Yiyang Xia, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/194,889

(22) PCT Filed: Jun. 4, 1997

(86) PCT No.: PCT/US97/09684

§ 371 (c)(1), (2), (4) Date: Aug. 23, 1999

(87) PCT Pub. No.: WO97/46249

PCT Pub. Date: Dec. 11, 1997

Related U.S. Application Data

(60) Provisional application No. 60/018,972, filed on Jun. 4, 1996.

(51) Int. Cl.
*A01N 38/00* (2006.01)
*A61K 39/00* (2006.01)
*C07K 14/00* (2006.01)

(52) U.S. Cl. ............... 514/2; 424/198.1; 530/351

(58) Field of Classification Search ............ 530/350, 530/345, 351, 889.2; 514/48, 12, 2; 424/85.1, 424/145.1; 435/7.1, 7.2
See application file for complete search history.

(56) References Cited

U.S. PATENT DOCUMENTS 5,935,810 A 8/1999 Friedman et al.
6,025,325 A * 2/2000 Campfield et al. ............ 514/2

FOREIGN PATENT DOCUMENTS

WO    WO 96/35787    11/1996

OTHER PUBLICATIONS

Bennett, et al., A role for leptin and its cognate receptor in hematopoiesis, 1996, *Current Biol.*, 6(9):1178-1180.
Gainsford, et al., Leptin can induce proliferation, differentiation, and functional activation of hemopoietic cells, 1996; *Proc. Natl. Acad. Sci.*, 93:14564-14568.
Roubenoff, et al., TNF-alpha and leptin in adjuvant arthritis (AA): implications for inflammatory cachexia, 1996, *Arthritis and Rheumatism*, 39(9) supplement, Abstract No. 302, p. s77.
Sarraf, et al., Multiple cytokines and acute inflammation raise mouse leptin levels: potential role in inflammatory anorexia, 1997, *J. Exper. Med.*, 185(1):171-175.

* cited by examiner

*Primary Examiner*—Eileen B. O'Hara
*Assistant Examiner*—Gyan Chandra
(74) *Attorney, Agent, or Firm*—Thomas Fitting; Michael J. McCarthy

(57) ABSTRACT

Compositions comprising OB-R agonists and methods of treatment for conditions such as systemic inflammatory response syndrome are provided. One suitable OB-R agonist ligand is recombinant human OB protein, also known as leptin. Also provided are methods and compositions for the treatment of obesity and OB resistance. Assay methods and kits relating to these conditions are also included.

5 Claims, 16 Drawing Sheets

DIAGNOSTIC AND THERAPEUTIC METHODS RELATED TO REGULATING ENERGY MOBILIZATION WITH OB PROTEIN AND OB ANTIBODIES

CROSS REFERENCE TO RELATED APPLICATION

This application claims the benefit of U.S. Provisional Application Ser. No. 60/018,972, filed Jun. 4, 1996, which is incorporated by reference, as are all references cited herein.

GOVERNMENTAL RIGHTS

This invention was made with government support under Contract No. DK 20043 by the National Institutes of Health. The government has certain rights in the invention.

BACKGROUND OF THE INVENTION

The obese gene in human, rat and mouse encodes a protein hormone having an open reading frame 167 amino acid residues in length, called leptin, also known as OB protein or the ob gene product. Removal of the signal sequence yields a mature secreted 16 kilodalton protein that is 146 amino acid residues in length.

OB protein is produced primarily by adipocytes of white adipose tissue (WAT). OB protein is secreted directly into the extracellular space and travels through the blood stream. OB protein affects the cells of its target organs by binding to the OB receptor protein, OB-R, that is found on the extracellular surface of the plasma membrane of target cells. Binding of OB protein to OB-R activates the intracellular second messenger cascade of the JAK-STAT system, which is characteristic of activation of cytokine type I receptors.

OB protein is produced in adipocytes in proportion to the mass of stored fat, thereby providing a hormone signal for a lipostatic feedback circuit, which is mediated by the OB receptor. While OB proteins of different species show a close similarity in their sequences, the sequences of OB proteins are not closely similar to other types of proteins. For example, the human ob gene sequence and its mouse homologue (85% sequence identity) have been reported to have no sequence similarity to other proteins of known structure (DiFrancesco, V., et al., Protein Topology Recognition from Secondary Structure Sequences: Application of the Hidden Markov Models to Alpha Class Proteins, *J. Mol. Biol.* 267: 446–463 (1997) at page 457).

Although OB protein is composed of a single peptide chain, an intrachain disulfide bond between cysteine 96 and cysteine 146 is required both to stabilize the conformation of the molecule and to confer in vivo biological activity (Rock, F. L., et al., The Leptin Haemopoietic Cytokine Fold is Stabilized by an Intrachain Disulfide Bond, *Horm. Metab. Res.* 28: 649–652 (1996)). It is believed that the special geometry of the A and D major helices must be maintained in order to dock to a conserved receptor trough in the receptor molecule, a requirement that produces structural similarity between OB proteins and cytokines in the face of negligible sequence conservation (*Id.* at 651.).

One accepted and successful animal model of human obesity is the genetically obese mouse bearing the recessive obese mutation (ob/ob). The mouse model reproduces not only the human obesity condition, but also develops non-insulin dependent diabetes mellitus (NIDDM, also known as type II diabetes mellitus). Homologous obese genes have been described in mouse, rat and human.

The mouse is also a widely accepted and successful model of sepsis, septic shock and systemic inflammatory response syndrome (SIRS), a term which describes the clinical syndrome of sepsis without regard to its cause. Simple models, involving a large bolus dose of lipopolysaccharide (LPS) administered to mice and using mortality as the primary outcome variable, are well suited for preliminary pharmacological studies of new drugs or other therapeutic agents (Fink, M. P. & Heard, S. O., Laboratory Models of Sepsis and Septic Shock, *J. Sure. Res.* 49: 186–196, 1990, at 188–189).

Both the ob gene (Zhang, Y., et a, Positional cloning of the mouse obese gene and its human homologue, *Nature* 372: 425–432 (1994); accession No. U18812, SEQ ID NO. 1) and its receptor (Tartaglia, L. A., et al., Identification and expression cloning of a Leptin Receptor, *Cell* 83: 1263–1271 (1995); Chen, H., et al., Evidence that the Diabetes Gene Encodes the Leptin Receptor: Identification of a Mutation in the Leptin Receptor Gene in db/db Mice *Cell* 84: 491–495 (1996); accession No. U46135, SEQ ID NO. 2) have been cloned. Shorter versions of the OB receptor, termed the OB-Ra, OB-Rc and OB-Re forms, are produced by alternative splicing of the OB-R mRNA (Lee, G. H., et al. *Nature* 379: 632–635 (1996)). The full length OB receptor is called the OB-Rb form.

Neural activity in specific regions of the central nervous system (CNS), such as the hypothalamus, controls processes related to food intake and energy expenditure. The cloning of the OB protein gene and the OB receptor gene and the localization of OB receptor expression in the hypothalamus has provided supporting evidence for this view as well as suggesting possible mechanisms for relating food intake to stored fat reserves. The OB protein is produced by adipocytes in proportion to the mass of stored fat and, hence, it acts as the signal to a lipostat control circuit. This lipostat signal is transduced at the target cells by the OB receptor, OB-R, in the CNS, resulting changes in neural activity that regulate both food intake and metabolic rate.

Metabolic derangement is an important characteristic of the host response to critical illness called the acute phase response that characterizes conditions such as sepsis and septic shock (Kushner, I. *Ann. N.Y. Acad. Sci.* 389: 39–48 (1982)). Hypothermia is a metabolic response that may be pertinent clinical prognostic factor in systemic inflammatory response syndrome in humans (Brivet, F., et al. *Crit. Care Med.* 22: 533–534 (1994)).

There is a need for at least one disease marker for systemic inflammatory response syndrome (SIRS) and related conditions. Hereinafter, the term SIRS is used to denote sepsis, septic shock, sepsis syndrome, and related conditions. Disease markers have numerous functions. In this case, a marker for SIRS would be useful for predicting the development of SIRS, identifying patients with SIRS, predicting outcome, aiding timing and targeting of therapeutic interventions, and determining the pathogenesis of SIRS in patients (Parsons, P. E. & Moss, M. Early Detection and Markers of Sepsis, *Clinics in Chest Medicine* 17:199–212 (1996)).

SUMMARY OF THE INVENTION

Embodiments of the present invention include compositions and methods for treating a patient having a condition in which regulating energy metabolism during a systemic inflammatory response is desired, comprising administering a composition having a physiologically effective amount of at least one OB-R agonist ligand. Suitable OB-R agonist ligands include recombinant OB protein, peptide conformational analogs of human OB protein comprising conservative substitutions of amino acid residues and OB-related peptides. A preferred OB-R agonist ligand is recombinant human OB protein.

In another therapeutic embodiment, the beneficial aspects of OB-R agonist ligand administration are facilitated by a coordinated increase in the number of OB receptors (OB-R) produced by the administration of agents that OB-R expression inducers. Suitable OB-R expression inducers include lipopolysaccharide (LPS) and cytokines. Preferred cytokines are interleukin-1α (IL-1α), interleukin-1β (IL-1β), tumor necrosis factor-α (TNF-α) and interleukin 6 (IL-6). Particularly preferred cytokines are IL-6 and IL-1β.

In a further therapeutic embodiment, antibodies to OB protein are used as agents capable of blocking the effects of OB receptor activation, especially fat mobilization and increased energy utilization. Suitable antibodies to OB proteins may be polyclonal or monoclonal. Suitable antibodies comprise immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab' and F(ab')$_2$. This embodiment is suitable for treating metabolic derangement due to conditions such as anorexia, amenorrhea, cachexia and the like.

Antibodies to OB protein are also useful as an assay kit and method for detecting the level of OB protein in a patient. The level of OB protein in a patient is a disease marker that is useful for predicting the development of a condition, identifying patients with the condition, predicting outcome of the condition, aiding timing and targeting of therapeutic interventions, and determining the pathogenesis of the condition in patients. Conditions in which the level of OB protein is a useful marker are SIRS and related conditions such as sepsis and septic shock, as well as anorexia, amenorrhea, cachexia and the like.

DETAILED DESCRIPTION OF THE PREFERRED EMBODIMENTS

Figure 1:
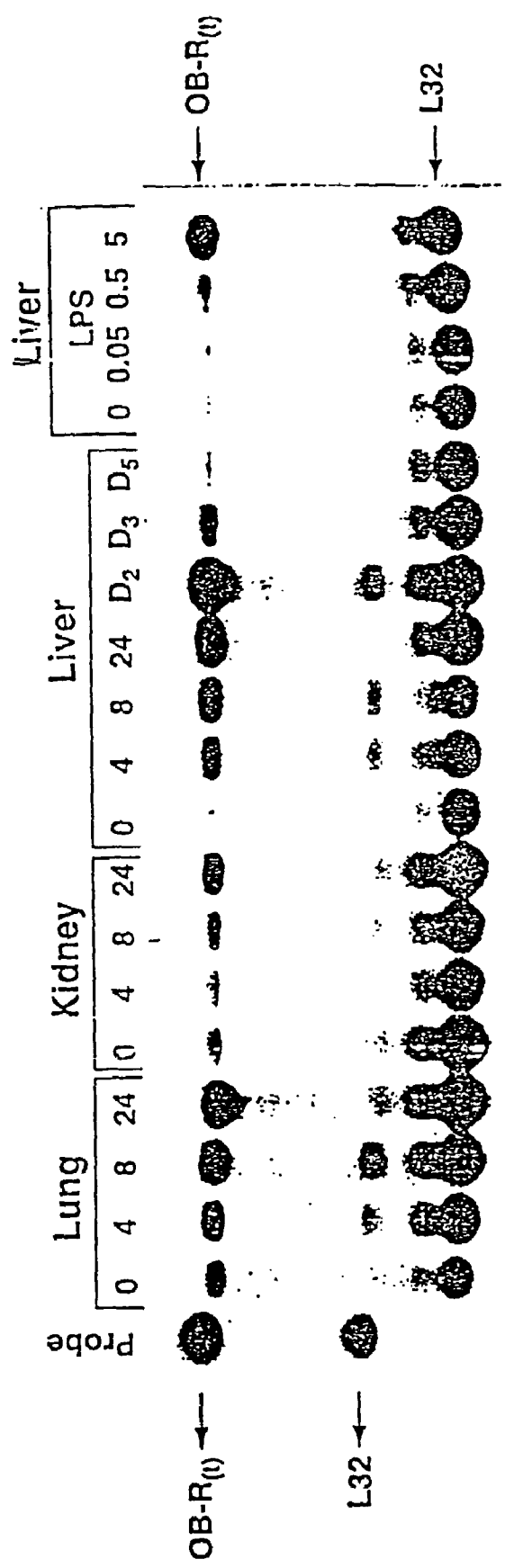
FIG. 1 is a representation of an autoradiogram showing the results of a ribonuclease (RNase) protection assay showing expression of total OB receptor (OB-R$_{(t)}$) in lung, kidney and liver at 0, 4, 8 or 24 hours, or 2 (D$_2$), 3 (D$_3$) or 5 (D$_5$) days after intravenous injection of 5 µg per gram of body weight as well as a dose-response study showing the relative effects on the liver the of injection of 0.05, 0.5 or 5 µg of LPS per gram of body weight.

It has been found that substances that initiate or mediate SIRS, for example, LPS and several cytokines, induce the increased expression of OB-R in liver and other peripheral tissues. Thus, occupancy and activation of OB-R by an agonist ligand such as recombinant OB protein, OB-related peptides or peptide conformational analog of human OB protein comprising conservative substitutions of amino acid residues serves as a protective homeostatic mechanism in systemic inflammatory response syndrome conditions such as endotoxic shock, sepsis and septic shock. A preferred OB-R agonist ligand is recombinant OB protein. Suitable therapeutic human doses of recombinant OB protein are from about 1 micrograms per kilogram body weight to about 50 microgram per kilogram body weight. One preferable therapeutic human dose is about 10 micrograms per kilogram body weight.

While the regulation of energy homeostasis is essentially a function of the CNS, food intake and the majority of the energy expenditure take place in peripheral organs such as the liver. It has been found that the OB protein and the OB receptor have a functional involvement in peripheral energy homeostasis. In general, critical illness and trauma can dramatically alter metabolism, with the expression of the OB receptor changing in response to pathological stress. The expression of OB-R in liver and other peripheral organs, but not in the central nervous system, has now been shown to be induced by endotoxic shock produced intravenous injection of cytokines, such as, IL-1β, TNF-α and IL-6, as well as cytokine inducing agents such as LPS, into mice, an accepted animal model of SIRS and related conditions. OB protein, antibodies to OB protein, and OB-R expression inducers are useful for the diagnosis and treatment of conditions such as sepsis, systemic inflammatory response syndrome, cachexia and anorexia.

The administration of recombinant mouse OB protein to mice following OB-R induction with a normally lethal dose of LPS conferred complete resistance to LPS, resulting in survival. The OB-treated mice maintained a higher body temperature and displayed dramatic weight loss in contrast to control counterparts. In vivo administration of OB antisera, on the other hand, elicited the opposite effects by blocking OB-mediated processes, thereby stimulating postprandial food intake leading to rapid weight gain. Co-administration of LPS with a second in vivo treatment with OB antisera, however, resulted in 100% mortality as compared to animals treated with control antisera.

OB protein, in mediating host responses to LPS-induced endotoxemia, exerts its protective effect primarily by initiating energy mobilization and heat production in critical conditions, the effect of which is proportional to the level of OB protein in the blood. By altering the levels of OB protein, the amount of energy mobilized to resist challenges induced by inflammatory agents is correspondingly altered, thereby effecting the ultimate inflammatory response.

Therefore, in view of the newly discovered physiological properties of OB protein and OB antibodies in regulating energy mobilization and consumption, the present invention describes both diagnostic and therapeutic methods relating to the use of recombinant human OB protein and antibodies thereto in modulating the effects of OB-R activation in vivo.

Diagnostic Applications

OB antibodies are useful for detecting the amount of OB present in sample taken from a patient. One preferred diagnostic embodiment is the use of OB antibodies for detecting the amount of OB present in a blood sample taken from a patient exhibiting a SIRS condition such as sepsis, septic shock, and the like. Such measurements of OB levels in vitro in blood sample by antibody detection is also indicated in various wasting conditions or syndromes associated with several disease states or syndromes, including anorexia, amenorrhea, cachexia, chronic inflammatory conditions, AIDS and AIDS-related conditions, as well as sepsis, septic shock, SIRS and the like. Alternatively, the determination of OB levels is useful in systemic inflammatory response syndromes (SIRS) that are characterized by an acute increase in inflammatory mediators, such as IL-1β, Il-6, TNF, LPS and the like. Such conditions are noted in preoperative patients subject to fasting, in patients with acute injuries such as burns or trauma, in patients with SIRS, or with ongoing bacterial infections or those receiving TNF-α for treatment of tumors and in persons suffering from hypothermia.

While there is little sequence similarity between OB proteins and other molecules, the three-dimensional conformation of the OB protein molecule is analogous to that of several long-chain helical cytokines: four major alpha helix regions, A–D, connected by short loops and minor helical regions (Zhang, F., et. al., Crystal Structure of the obese protein leptin-E100, *Nature* 387: 206–209 (1997)).

As used herein, a conformational analog of OB protein is a molecule having substantially the same conformational characteristics of its three-dimensional structure that are required for activation of the OB receptor. Examples of such conformational characteristics include the conformation of the A major helix, the conformation of the D major helix, and the disulfide bond that maintains the geometrical relationship between the A and D major helices. Thus, amino acid substitutions that conserve the conformational characteristics of the molecule, for example, in the loop regions connecting the major helices, would produce conformational analogs to OB protein.

Peptides derived from the region of the OB protein from amino acid residues 106 to 140, as short as about 15 amino acids long, have been shown to be effective in mimicking the action of full-length recombinant OB protein (Grasso, P., et al., In vivo Effects of Leptin-Related Synthetic Peptides on Body Weight and Food Intake in Female ob/ob Mice: Localization of Leptin Activity to Domains Between Amino Acid Residues 106–140, *Endocrinology* 138: 1413–1418 (1997)). As used herein, "OB-related peptides" refers to natural or synthetic peptides derived from the region of the OB protein from about amino acid residue 106 to about amino acid residue 140 and includes conservative amino acid residue substitutions.

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab' and F(ab')$_2$. An antibody composition of the present invention is characterized as containing antibody molecules that immunoreact with OB protein or portions thereof.

An antibody composition of the present invention is typically produced by immunizing a mammal with a inoculum of OB protein or some fragment of OB protein, alone or in combination with a suitable adjuvant such as Freund's adjuvant, and thereby induce in the mammal antibody molecules having the appropriate immunospecificity. The antibody molecules are then collected from the mammal and isolated to the extent desired by well known techniques such as, for example, immunoaffinity chromatography. The antibody composition so produced can be used, inter alia, in the diagnostic methods and systems of the present invention or in the preparation of therapeutic compositions of the present invention.

Monoclonal antibody compositions can also be used with the present invention. A monoclonal antibody composition contains, within detectable limits, only one species of antibody combining site capable of effectively binding to OB protein. Thus, a monoclonal antibody composition of the present invention typically displays a single binding affinity for OB protein even though it may contain antibodies capable of binding proteins other than OB protein. Preferred monoclonal antibodies are those that bind to portions of the OB protein that are required for activation of the OB receptor, such as the A helix, the D helix, or regions of OB protein that maintain the relative positions of the A and D helices that are required for the activation of the OB receptor. Monoclonal antibodies against human OB protein have been described and their preparation was discussed in (Tsuruo, Y. et. al., *Horm. Metab. Res.* 28: 753–755 (1996). Monoclonal antibodies are also supplied commercially from vendors on a custom order basis (e.g., Alpha Diagnostic International, Inc., San Antonio, Tex.). Purified polyclonal anti-OB antibodies are commercially available from several sources (R&D Systems, Minneapolis, Minn.; Research Diagnostics, Inc., Flanders, N.J.; Linco Research, Inc., St. Charles, Mo.; Affinity BioReagents, Inc., Golden, Colo.).

Determination of OB levels with OB antibodies is performed by assay methods, including ELISA, radioimmunoassay (RIA), Western blot analysis, and the like, that are familiar to one of ordinary skill in the art. The determined OB protein levels are then compared to normal levels for the state of the patient, e.g., fasting, time of day, body mass index (BMI), aerobic conditioning, gender, etc. For example, the normal range found for lean males at 8 a.m. was 12.0±4.4 ng/ml (Sinha, M. K., et al., Nocturnal Rise of Leptin in Lean, Obese, and Non-Insulin-dependent Diabetes Mellitus Subjects, *J. Clin. Invest.* 97: 1344–1347 (1996)). See, also Horn, R. et al., Radioimmunoassay for the detection of leptin in human serum, *Exp. Clin. Endocrinol. Diabetes* 104: 454–458 (1996); McGregor, G. P., et al., Radioimmunological Measurement of Leptin in Plasma of Obese and Diabetic Human Subjects, *Endocrinology* 137: 1501–1504 (1996). It has recently been found that OB protein is present in the circulation in both bound and free form, and that the ratio of the two forms is different in lean and obese subjects (Sinha, M. K., et al., Evidence of Free and Bound Leptin in Human Circulation. Studies in Lean and Obese Subjects and During Short-Term Fasting, *J. Clin. Invest.* 98: 1277–1282 (1996)). The relation of free and bound forms to OB protein biological activity can be considered in the context of OB protein assays.

In an alternative embodiment, immunohistochemical assay of OB-R receptor numbers are performed on tissue biopsy materials using standard protocols. A preferred tissue biopsy is liver biopsy.

Therapeutic Applications

Embodiments of the present invention, including methods of administering to a patient compositions comprising OB-R agonist ligands are useful in treating conditions in which it is desirable to regulate or modify energy metabolism during a systemic inflammatory response. Suitable OB-R agonist ligands include recombinant OB protein, peptide conformational analogs of human OB protein comprising conservative substitutions of amino acid residues and OB-related peptides. A preferred OB-R agonist ligand is recombinant human OB protein. A suitable dosage range for recombinant human OB protein is from about 1 microgram per kilogram body weight to about 50 micrograms per kilogram body weight. OB-related peptides are used in a dosage range from about 0.1 microgram per kilogram body weight to about 5 micrograms per kilogram body weight, adjusting the dosage to account for art-recognized differences in potency and solubility (Grasso, P. et al., (1997)).

In a related embodiment, compositions comprising at least one OB-R expression inducer are useful for treating obesity and conditions in which there is an insufficient number of OB receptors, in which low copy number of OB receptors is a limiting factor or in which there is "OB resistance," i.e., a reduced effect of associated with a particular plasma concentration of OB protein.

In general, the OB-R expression inducer is administered in an amount from about 0.003 to about 20 micrograms per kilogram body weight. Suitable OB-R expression inducers include therapeutic cytokines used in cancer therapy, such as IL-1$\alpha$, IL-1$\beta$, IL-6 and TNF-$\alpha$. Suitable dosages and modes of administration are known in the art. For example, a suitable dosage ranges for IL-1$\alpha$ is about 0.1 to about 6 micrograms/m$^2$/day. A suitable dosage range for IL-1$\beta$ is about 3 to about 200 nanograms/kg/day. A suitable dosage range for IL-6 is about 0.5 to about 20 micrograms/kg/day, with a preferred dosage range for IL-6 being about 1 to about 5 micrograms/kg/day. The therapeutic cytokines may be administered singly or in combination. The mode of administration may be intravenous infusion over an extended time period or a single intravenous or subcutaneous injection. The daily dose may be administered as a single dose or divided into multiple dose given at intervals during the day.

In a further embodiment, to counteract the possible toxic side effects of OB-R expression inducers such as therapeutic cytokines, such substances are administered in a composition in combination with OB-R agonist ligands. Administration of such compositions is useful for conditions in with cytokines are normally administered for a therapeutic purpose such as tumor treatment, in order to provide effective protection by the OB-R agonist ligands from undesirable metabolic side effects. The up-regulation of the OB-R allows for the complete therapeutic effect mediated by OB-R agonist ligands such as OB protein. A suitable dosage range for recombinant human OB protein is from about 1 microgram per kilogram body weight to about 50 micrograms per kilogram body weight.

In an alternative embodiment, the present invention describes the administration of OB antisera, polyclonal or monoclonal, for treating conditions marked by increased OB and/or increased OB-R activity. Such conditions are various wasting conditions or syndromes associated with several disease states or syndromes, including anorexia, amenorrhea, cachexia, chronic inflammatory conditions, AIDS and AIDS-related conditions. A suitable dosage range for anti-OB protein antibodies is about 0.02 to about 15 milligrams/kg/day.

Figure 12:
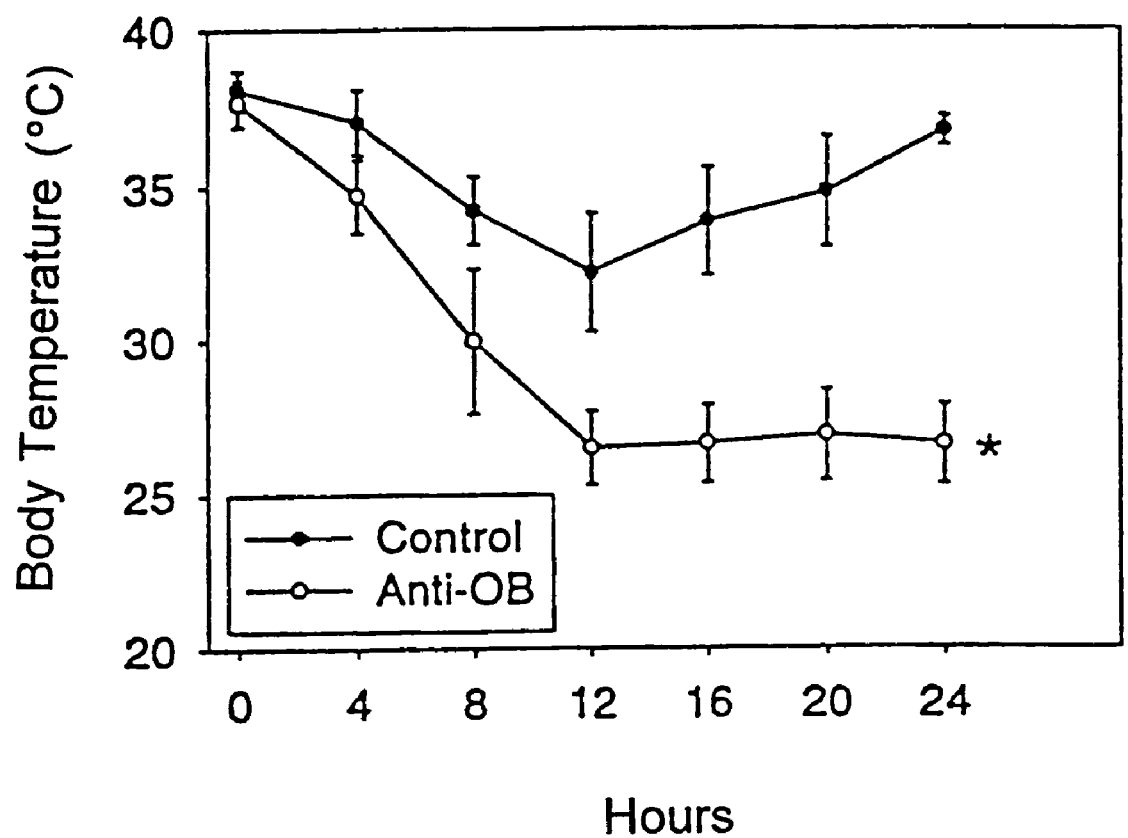
FIG. 12 is a graphical representation of the time course of the change in body temperature of mice that had received a LPS injection (6 µg per gram of body weight) after pretreatment with either anti-OB protein antiserum (anti-OB, N=16, except at * where N<16 due to mortality) or preimmune rabbit serum (control, N=16), data expressed as mean±S.E.M.
Figure 13:
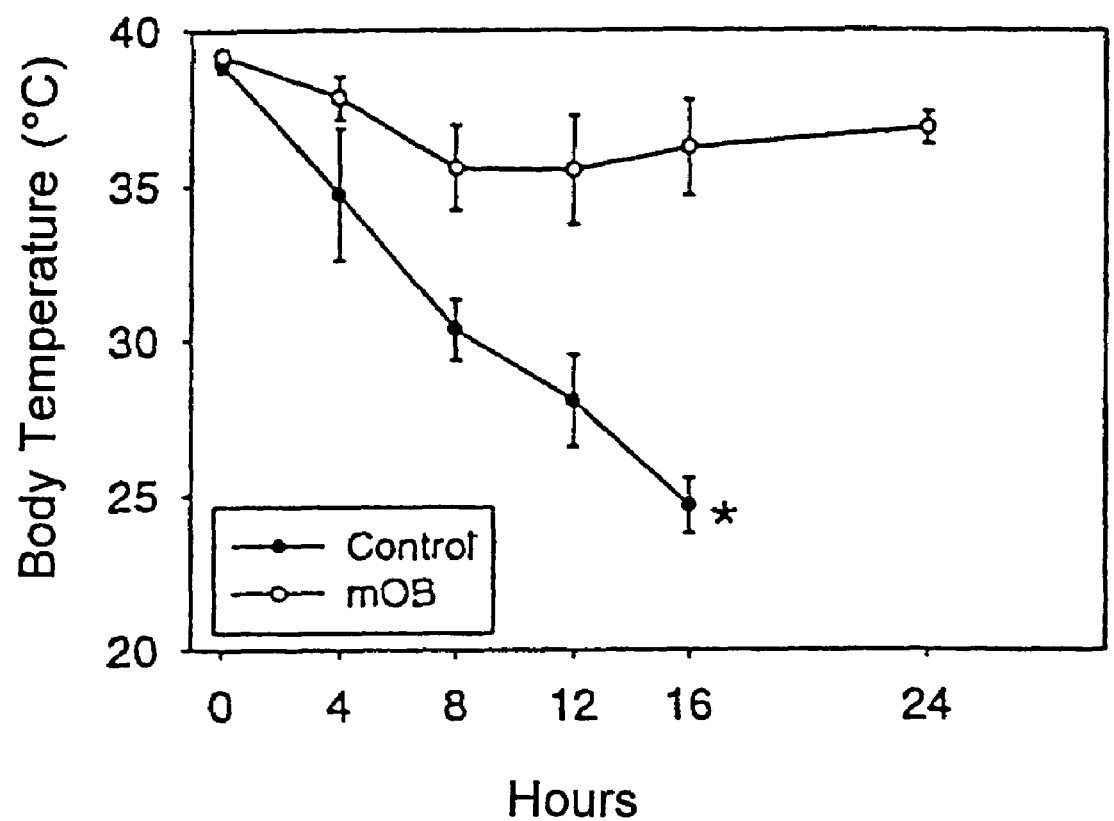
FIG. 13 is a graphical representation of the time course of the change in body temperature of mice that were treated with OB protein (mOB, N=16) or vehicle (control, N–16, except at * where N<16 due to mortality) after a LPS injection (10 µg per gram of body weight), data expressed as mean±S.E.M.
Figure 14:
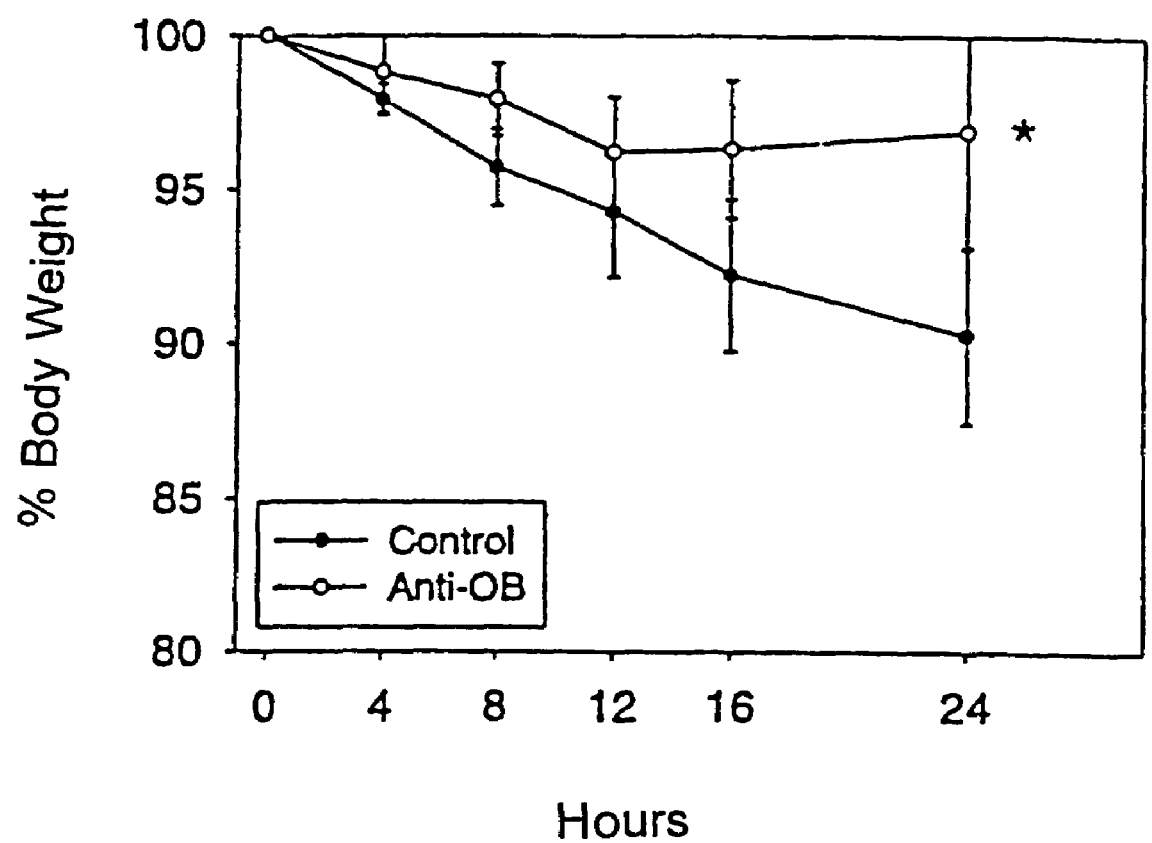
FIG. 14 is a graphical representation of the time course of the change in body weight (percent of initial body weight) of mice that had received a LPS injection (6 µg per gram of body weight) after pretreatment with either anti-OB protein antiserum (anti-OB, N=16) or preimmune rabbit serum (control, N=16, except at * where N<16 due to mortality), data expressed as mean±S.E.M.
Figure 15:
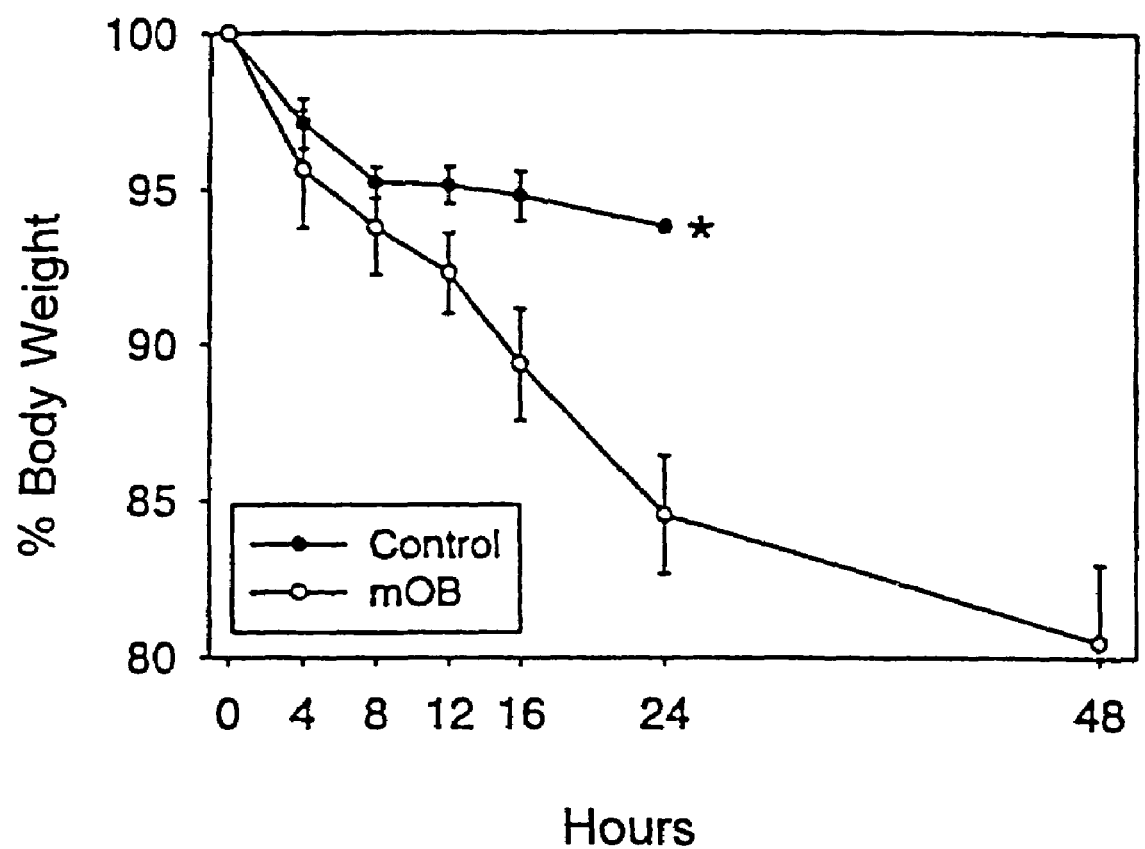
FIG. 15 is a graphical representation of the time course of the change in body weight (percent of initial body weight) of mice that were treated with OB protein (mOB, N=16) or vehicle (control, N=16, except at * where N<16 due to mortality) after a LPS injection (10 μg per gram of body weight), data expressed as mean±S.E.M.
Figure 16:
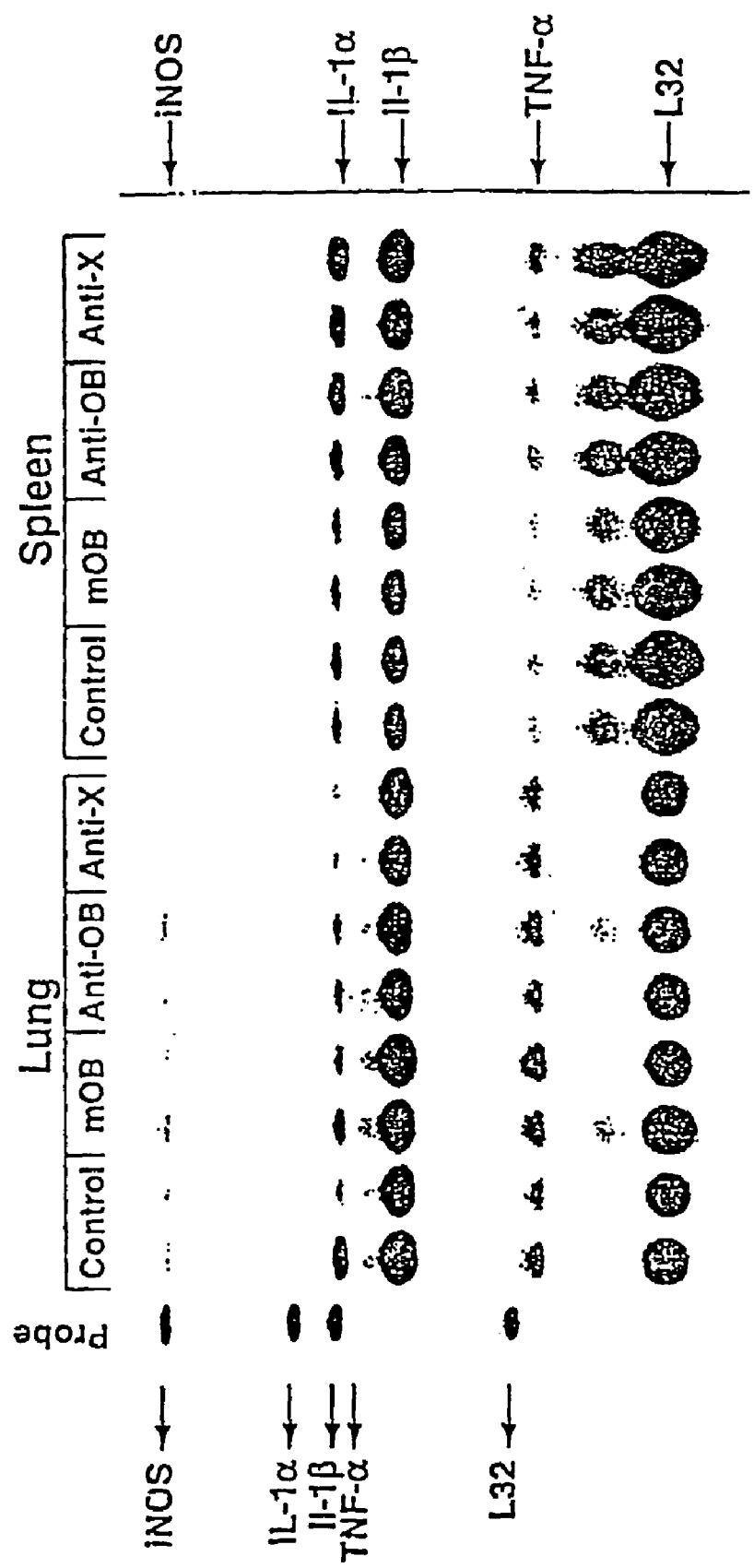
FIG. 16 is a representation of an autoradiogram showing the results of a RNase protection assay showing the expression of iNOS, IL-1α, IL-1β, and TNF-α mRNAs in mouse.

It has been found that OB protein is an important host defense factor against endotoxin stress. The protective effect of OB protein against endotoxin was not caused by suppressing the expression of major inflammatory mediators, since the mRNA levels of IL-1α, IL-1β, TNF-α, and iNOS in lung and spleen were similar in all LPS-treated mice regardless of the experimental manipulations (FIG. 16). A comparison of the four groups of mice revealed striking correlations among the OB protein available, the survival from endotoxin shock (FIGS. 10 and 11), the maintenance of body temperature (FIGS. 12 and 13), and the loss of body weight (FIGS. 14 and 15).

Anti-OB Ab-treated mice showed the least loss of body weight and had the most profound hypothermia even with a relatively low dose of LPS. Conversely, OB-treated mice receiving a high dose of LPS maintained a higher body temperature than those control mice that received less LPS. The OB-treated mice also had a greater weight loss than any reported in the literature (16% in the first 24 hours, compared with an average of 10% reported by other groups). The mice in these tests were age, sex and weight matched, fed the same diet, and, therefore, should have had very similar energy store. The different responses to endotoxemia described were likely due to differences in metabolic energy mobilization and dissipation, which, in turn, were attributed to the experimental manipulation of circulating OB protein levels.

When the level of circulating OB protein is varied, the energy mobilized to resist endotoxin challenge is correspondingly altered, and the outcome of the host response to endotoxin stress is affected. ob/ob mice, lacking OB protein due to a mutation in the ob gene, were very sensitive to LPS insult: a dose as low as 2 μg per gram of body weight caused a rapid fall of body temperature and death.

The results also suggest the existence of two pathways of thermogenesis and thermostasis. Anti-OB Ab treatment per se did not cause hypothermia in normal mice, suggesting that the thermostasis under non-pathological conditions was largely OB protein-independent. However, when given LPS, the anti-OB Ab-treated mice developed profound hypothermia, indicating that the thermogenesis in response to endotoxemia had become OB protein dependent. A corollary of this model is that genetic defects affecting the OB/OB-R pathway will have a severe hypothermic response to endotoxin. Indeed, db/db mice which carry a mutation in the OB-R gene, responded to a low dose of LPS injection in a manner very similar to that seen in ob/ob mice (data not shown), despite their increased level of OB expression.

EXAMPLE 1

Induction of OB-R Expression by Administration of LPS

The injection of LPS and cytokines, substances that are associated with sepsis, septic shock or SIRS caused increases in the expression of the OB receptor in peripheral organs such as liver, but not in brain.

Intravenous injection of lipopolysaccharide (LPS), IL-1β, TNF-α and IL-6 to mice induced OB receptor expression in the liver and other peripheral organs, but not in the central nervous system (CNS). To investigate the functional significance of the increased OB-R expression, an anti-OB antiserum was used to neutralize endogenous OB protein in mice prior to an LPS injection. The neutralization of OB protein led to profound hypothermia, insignificant loss of body weight, and death in mice in response to an otherwise nonlethal dose of LPS. Conversely, mice administered recombinant mouse OB protein became more resistant to LPS and survived an otherwise lethal dose. The OB protein-treated mice maintained a relatively high body temperature and displayed a dramatic weight loss. These results suggest that OB protein may promote energy mobilization to compensate for the increased energy consumption in endotoxemia, and that the OB/OB-R pathway may play an important role in critical host responses to inflammatory stress.

Methods:

In general, standard techniques or published modifications were used; see, generally, Sambrook, J., et al., *Molecular Cloning A Laboratory Manual*, 2d Ed., Cold Spring Harbor Laboratory Press (1989). C57BL/6 mice, 5–8 weeks of age and 17–20 g of weight, were injected intravenously with either LPS (5 μg per gram of body weight, List Biological Laboratory, Campbell, Calif.), IL-1β (R&D Systems, Minneapolis, Minn.), IL-6 (2.5 μg, Pharmingen, San Diego, Calif.), or TNF-α (a gift from Genentech, San Francisco, Calif.). Animals were sacrificed at 0, 4, 8 or 24 hours, or 2, 3 or 5 days after the injection.

Tissue from various organs, including brain, liver and kidney, was dissected and snap-frozen in liquid nitrogen. Total RNA was prepared from the frozen tissues by a single-step method (Chomczynski, P. & Sacchi, N., Single-Step Method of RNA Isolation by Acid Guanidinium Thiocyanate-Phenol-Chloroform Extraction, *Analytical Biochemistry* 162: 156–159 (1987).

The RNase protection assays were carried out as previously described (Feng, L., et al., Alternative Splicing of the NC1 Domain of the Human α3(IV) Collagen Gene *J. Biol. Chem.* 269: 2342–2348 (1994); Xia, Y., et al., LPS-Induced MCP-1, IL-1β, and TNF-α mRNA Expression in Isolated Erythrocyte-Perfused Rat Kidney, *Am. J. Physiol.* 264: F774–F780 (1993)). A ten microgram aliquot of total RNA pooled from three similarly treated mice was used for each sample in the RNase protection assay. The stored pooled samples were dissolved in 10 μl of 80% formamide, 0.4 M NaCl, 1 mM EDTA, and 40 mM piperazine-N,N'-bis(2-ethanesulfonic acid), heated to 85 degrees Celsius for 5 minutes. Each ten microgram sample was then hybridized with about $1 \times 10^5$ cpm (counts per minute) of the appropriate [$^{32}$P]UTP-labeled antisense riboprobe at 55 degrees Celsius for at least 10 hours. The unhybridized RNA was then digested with 50 unit/ml RNase T1 (GIBCO/BRL, Gaithersburg, Md.) and 24 μg/ml RNase A at 30 degrees Celsius for one hour. The RNase was then digested with 625 μg/ml proteinase K (Boehringer Mannheim, Indianapolis, Ind.) for 30 minutes at 37 degrees Celsius. After phenol-chloroform extraction and sodium-acetate-ethanol precipitation, the protected hybridized RNA was denatured and electrophoresed on a 10% polyacrylamide gel. The gels were transferred to 3M Whatman filter paper, dried and exposed to Kodak X-Omat film. The resulting autoradiograms were developed in a Kodak X-Omat processor were used only for qualitative screening.

Radioactivity due to hybridization of target sequences with $^{32}$P-labeled riboprobes was quantified by scanning the gels on an AMBIS radioanalytic scanning system (AMBIS Systems, San Diego, Calif.).

An OB-Rb cDNA probe (from base 2548 to base 2835 of OB-Rb, Gen-Bank™ Accession No. U46135) was subcloned from a full-length mouse OB-Rb cDNA. The full-length mouse cDNA for the OB-R long form (OB-Rb) was cloned from a mouse hypothalamus cDNA library (Stratagene, La Jolla, Calif.), and the sequence was verified against that of U46135.

The full-length mouse cDNA for the OB-R short form (OB-Ra) was cloned from a mouse lung cDNA Library (Stratagene, La Jolla, Calif.). A 224 bp probe that included base 1250 to base 1474 (as indicated on the OB-Rb sequence) of OB-Ra was used for the RNase protection assay. This fragment, which comprises a sequence that is shared by all variants of OB-R, was used as a probe for the total level of OB-R ($OBR_{(t)}$).

The expression of other forms of OB-R mRNA was analyzed using selective probes for the respective different forms of OB-R. The designated probes provided full protection to their corresponding OB-R forms and partial protection for other OB-R forms. A probe derived from L32 (33–126, Gen-Bank™ Accession No. X06483), a housekeeping gene encoding ribosomal protein, was used as a control.

OB-Rc and OB-Re probes were cloned by reverse-transcription-PCR (RT-PCR) of total liver RNA from LPS-treated C57BL/6 mice. Protocols for RT-PCR are known in the art (for example, pages 15-13–15-15 of Ausubel, F. M., et al., *Short Protocols in Molecular Biology*, 2nd Edition, John Wiley and Sons, New York, (1992)).

One suitable protocol for RT-PCR is a modification of that previously described (Feng, L., et al., *J. Biol. Chem.* 269: 2342–2348, 1994). The primers used in RT-PCR are listed in Table 1, below. Primer oligonucleotides were synthesized using an ABI model 380B synthesizer (Applied BioSystems, Foster City, Calif.).

provided by the manufacturer or other standard protocols (e.g. Ausubel, F. M., et al., pages 4-18–4-21) with the appropriate (e.g., SP6 or T7) bacteriophage RNA polymerase. The riboprobes contained regions corresponding to the vector polylinker in addition to the region corresponding to the target sequence, and thus were longer than the protected bands. The mouse ribosomal L32 gene, a constitutively expressed "housekeeping" gene, was used throughout the study as a control.

Figure 6:
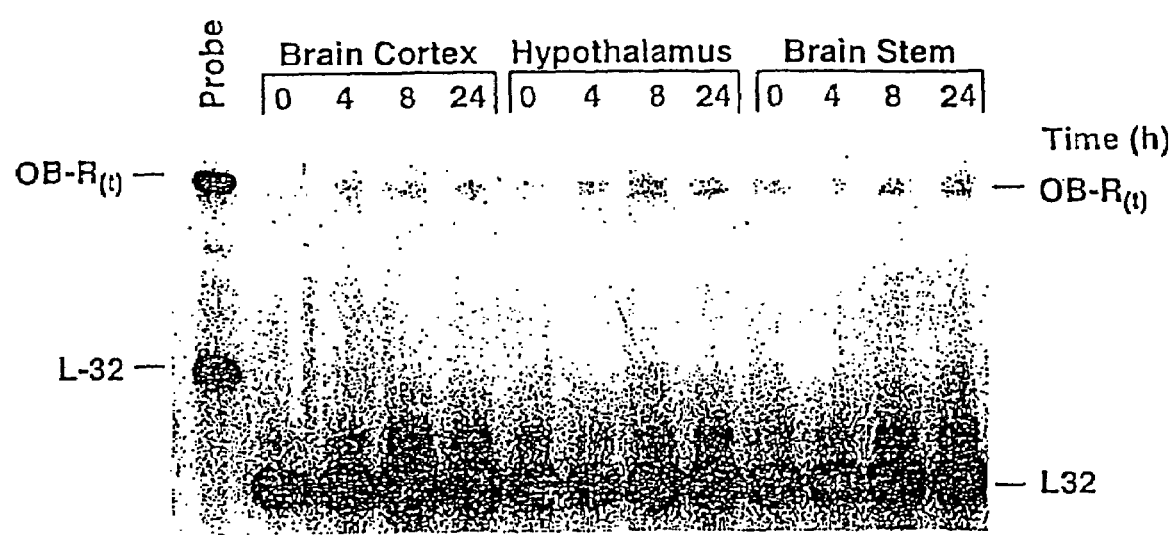
FIG. 6 is a representation of an autoradiogram showing the results of a RNase protection assay showing OB-R mRNA levels in brain cortex, hypothalamus, and brain stem at various times after LPS injection (5 µg per gram of body weight)
Figure 7:
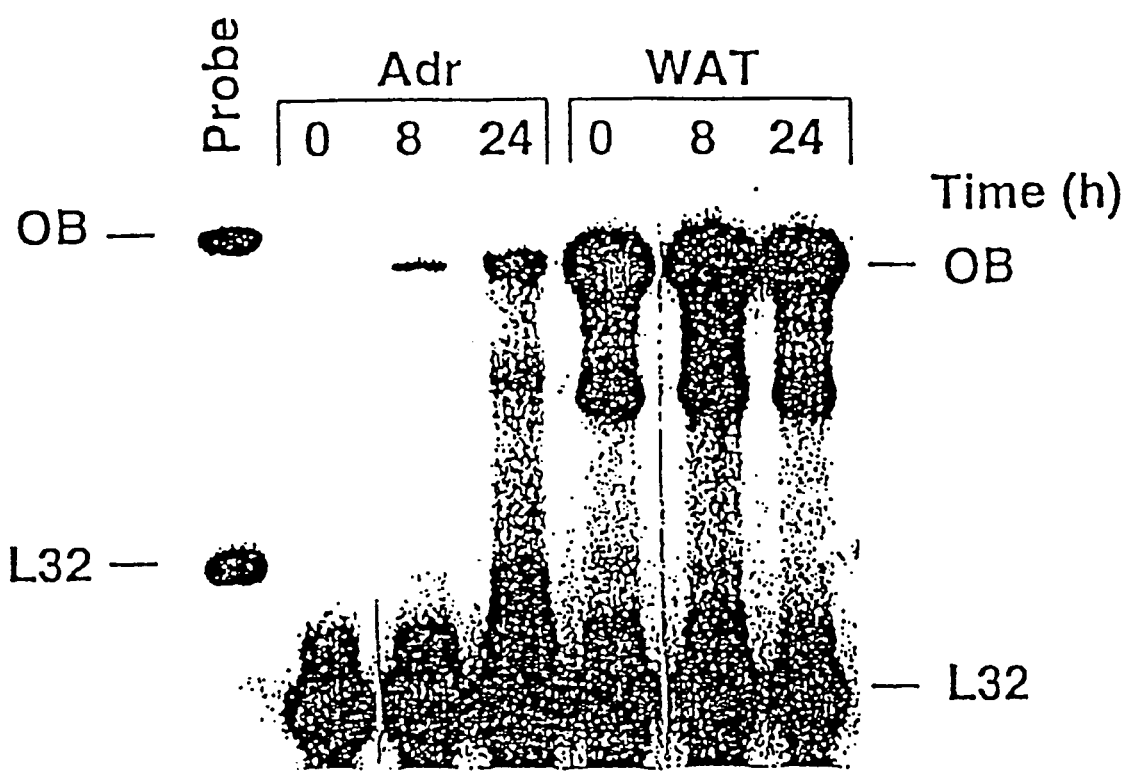
FIG. 7 is a representation of an autoradiogram showing the results of a RNase protection assay showing OB mRNA expression in the adrenal gland (Adr) and white adipose tissue (WAT) at various times after LPS injection (5 µg per gram of body weight)

Results:

When LPS was administered to C57BL/6 mice, a strong induction of total OB-R expression ($OB-R_{(t)}$) was detected in a number of peripheral organs (FIG. 1), but not in several areas of the central nervous system, such as the hypothalamus, that are known to express OB-R (compare FIG. 1 and FIG. 6). The increased expression of OB-R was most prominent in the liver, the major site of metabolic regulation. The increase of OB-R mRNA expression in the liver was LPS dose-dependent, and peaked between 24 and 48 hours post-LPS injection (FIG. 1).

Figure 2:
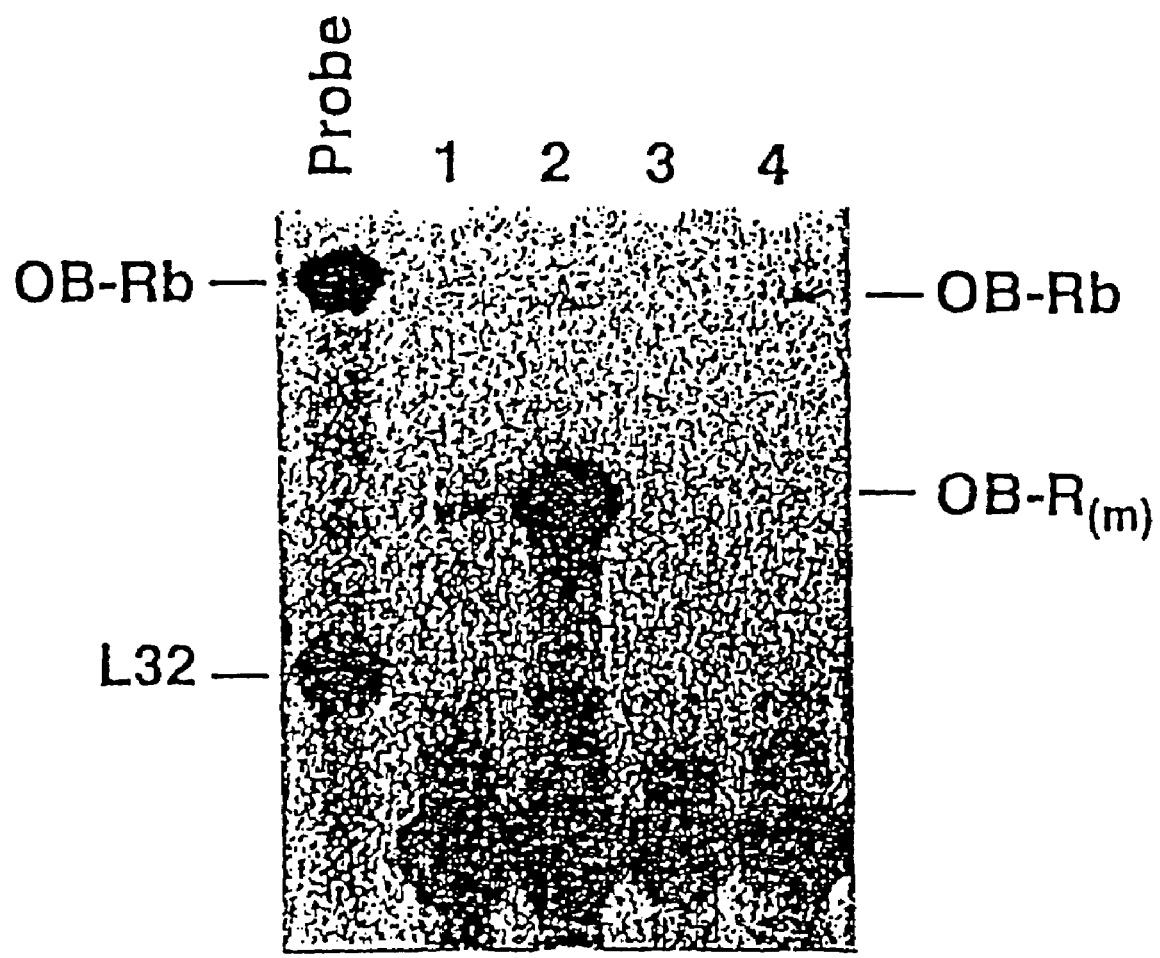
FIG. 2 is a representation of an autoradiogram showing of the results of a RNase protection assay showing expression of OB-Rb in normal liver (lane 1), and the LPS-treated liver at 24 hours (lane 2), and in the hypothalamus of normal control (lane 3) and ob/ob mice (lane 4), compared to OB-R$_{(m)}$) which represents the mixture of OB-R forms partially protected by the designated nucleotide probes.
Figure 3:
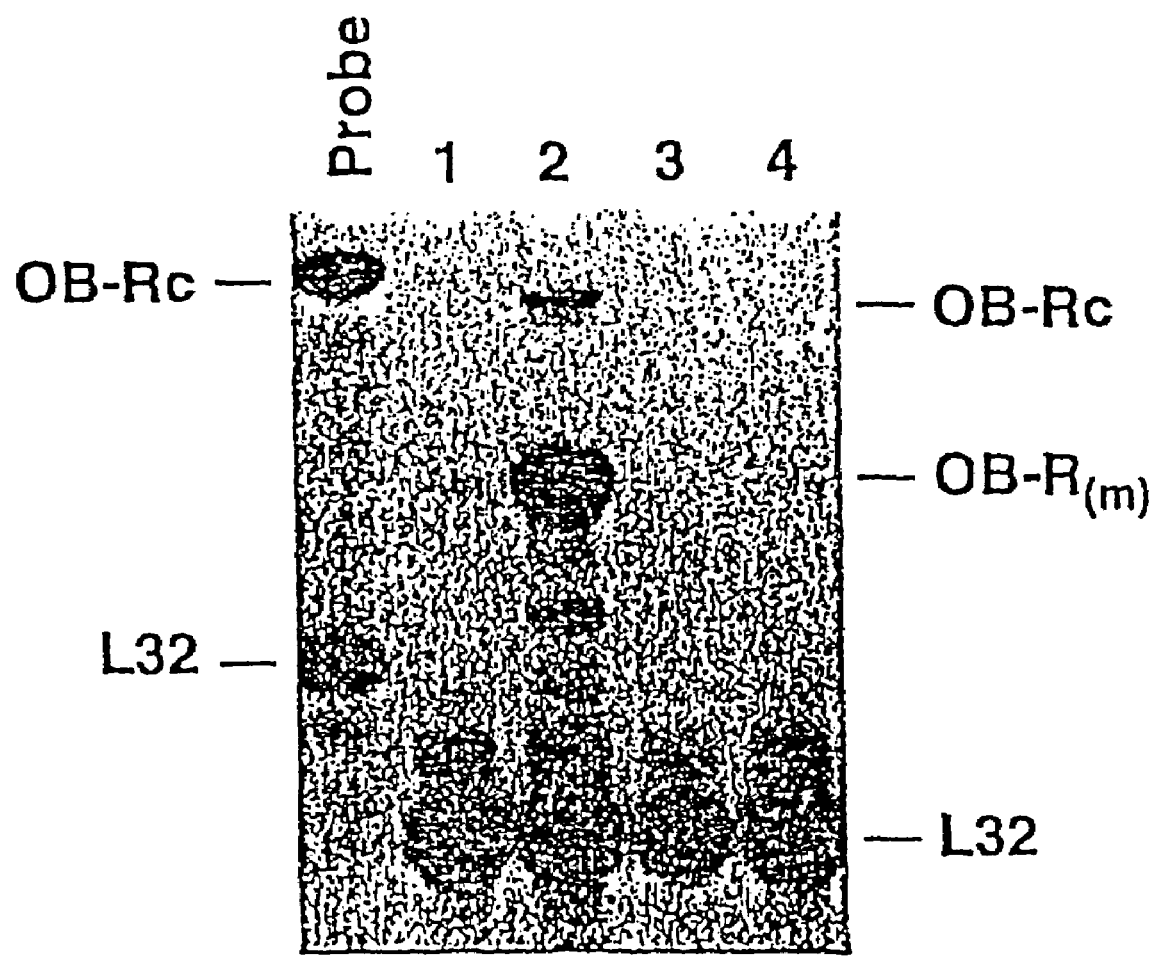
FIG. 3 is a representation of an autoradiogram showing the results of a RNase protection assay showing expression of OB-Rc in normal liver (lane 1), and the LPS-treated liver at 24 hours (lane 2), and in the hypothalamus of normal control (lane 3) and ob/ob mice (lane 4), compared to OB-R$_{(m)}$) which represents the mixture of OB-R forms partially protected by the designated nucleotide probes.

Unexpectedly, RNase protection assays using probes specific for alternatively spliced forms of OB-R mRNA revealed that the long form, OB-Rb, was also induced in the liver to a level comparable to that found in the ob/ob mouse hypothalamus and greater than that of the lean control mouse hypothalamus (FIG. 2). However, the majority of hepatic OB-R were the OB-Ra, OB-Rc (FIG. 3) and OB-Re (FIG. 4) forms. OB-Rd expression in the liver was undetectable (data not shown).

Figure 5:
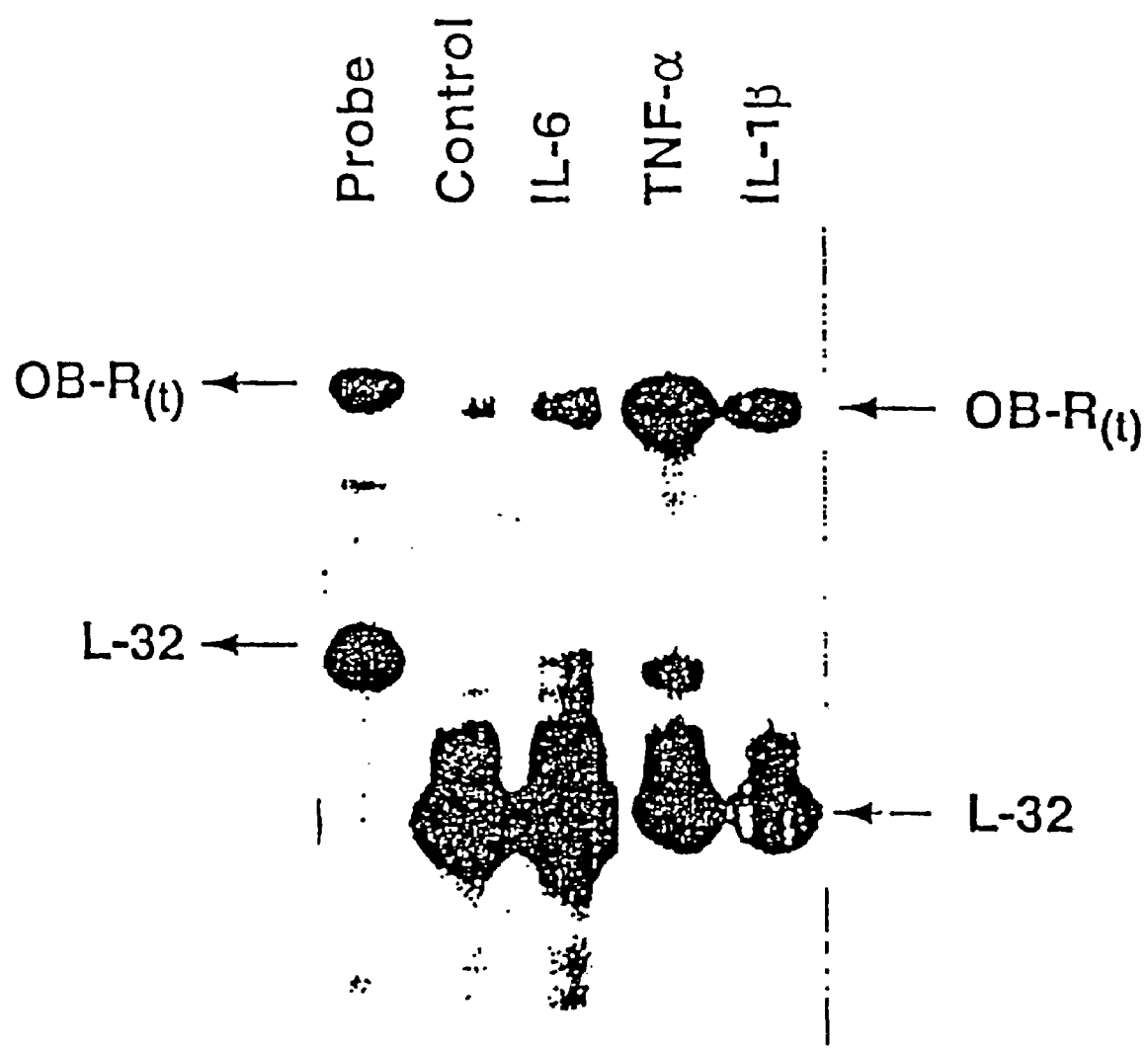
FIG. 5 is a representation of an autoradiogram showing the results of a RNase protection assay showing OB-R expression in mouse liver 24 hours after IL-6 (2.5 µg per mouse), TNF-α (10 µg per mouse) and IL-1β, (5 µg per mouse) injection.

In addition to LPS, OB-R expression was induced by the cytokines IL-6, IL-1α and TNF-α (FIG. 5). Contrary to a recent report (12), we found no detectable increase in OB

TABLE 1

PCR Primers

| | Sequence | |
|---|---|---|
| OB-Rc sense | 5'-GCTATCGACAAGCAGCAGAAT-3' | (SEQ ID NO. 8) |
| OB-Rc antisense | 5'-TGAACACAACAACATAAAGCCC-3' | (SEQ ID NO. 9) |
| OB-Re sense | 5'-TGTTATATCTGGTTATTATTGAATGG-3' | (SEQ ID NO. 10) |
| OB-Re antisense | 5'-CATTAAATGATTTATTATCAGAATTGC-3' | (SEQ ID NO. 11) |

First strand cDNA synthesis was performed using total liver RNA from LPS-treated C57BL/6 mice and murine leukemia virus reverse transcriptase with a random hexanucleotide primer. The 100 μl reaction mixture contained standard enzyme buffer, 5 μg of total RNA, 20 units of RNasin (RNase inhibitor), 500 pmol of hexanucleotide primer, 10 mM dithiothreitol, 1 mM of each dNTP, with 200 units of reverse transcriptase. Each reaction mixture was heated to 95 degrees Celsius for 10 minutes. PCR was then performed with separate aliquots of the reaction mixture with the appropriate primers for 35 cycles, using 60 degrees Celsius for annealing.

Figure 4:
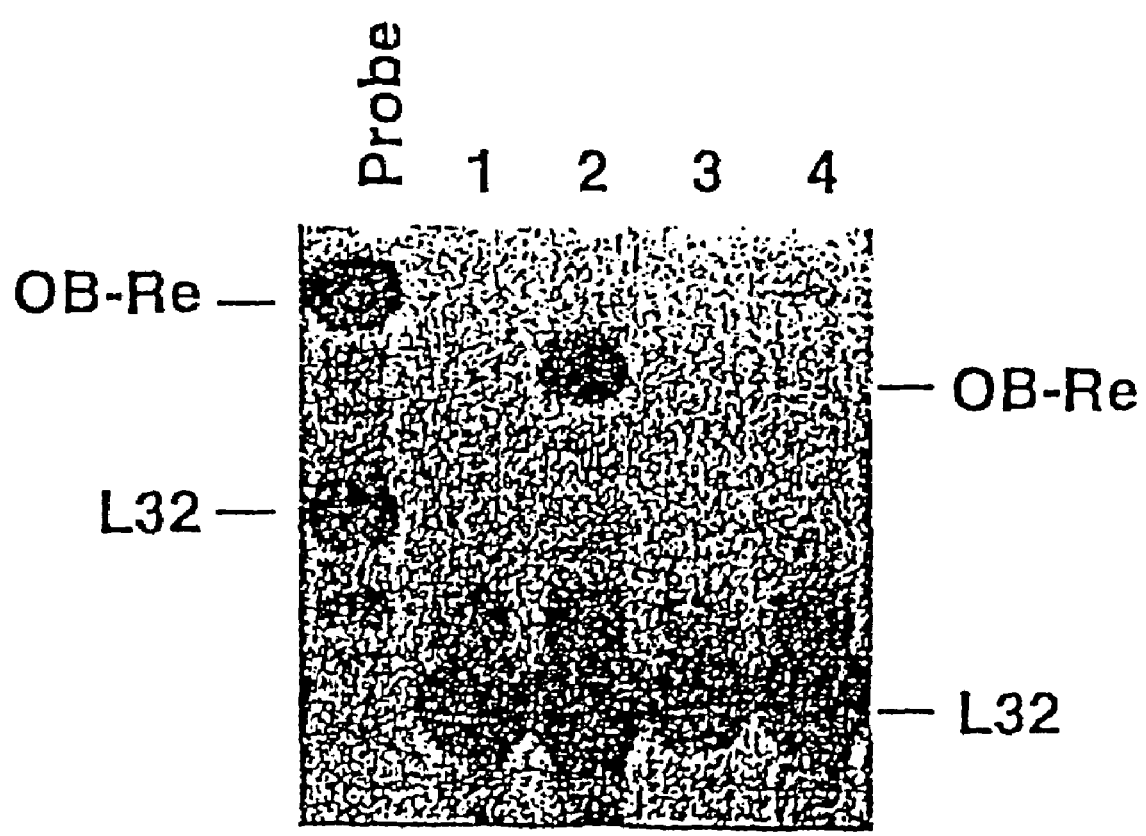
FIG. 4 is a representation of an autoradiogram showing the results of a RNase protection assay showing expression of OB-Re in normal liver (lane 1), and the LPS-treated liver at 24 hours (lane 2), and in the hypothalamus of normal control (lane 3) and ob/ob mice (lane 4), compared to OB-R$_{(m)}$) which represents the mixture of OB-R forms partially protected by the designated nucleotide probes.

The cDNA segments used to generate riboprobes were excised by the appropriate restriction endonucleases and subcloned into the multiple cloning site of a standard transcription vector. Suitable transcription vectors include a vector chosen from the pGEM series (Promega, Madison, Wis.). Labelled single stranded riboprobes were synthesized using standard in vitro transcription protocols, either those expression in white adipose tissue in LPS-treated mice, but detected a distinct induction of OB mRNA expression in the adrenal gland (FIG. 4). No OB mRNA expression was found in the brain, heart, lung, liver, kidney, spleen, muscle, stomach, duodenum, jejunum, ileum, or colon of LPS-treated mice (data not shown).

EXAMPLE 2

Production of Recombinant OB Protein

Recombinant OB protein was expressed in *E. coli* using a prokaryotic expression vector and extracted from inclusion bodies. Other vectors and host cells systems, including eukaryotic cells, are known in the art and also suitable for the expression of OB protein. See, generally, Ausubel, F. M., et al. *Short Protocols in Molecular Biology* 2nd Ed., pages 16-1 to 16-89.

Figure 8:
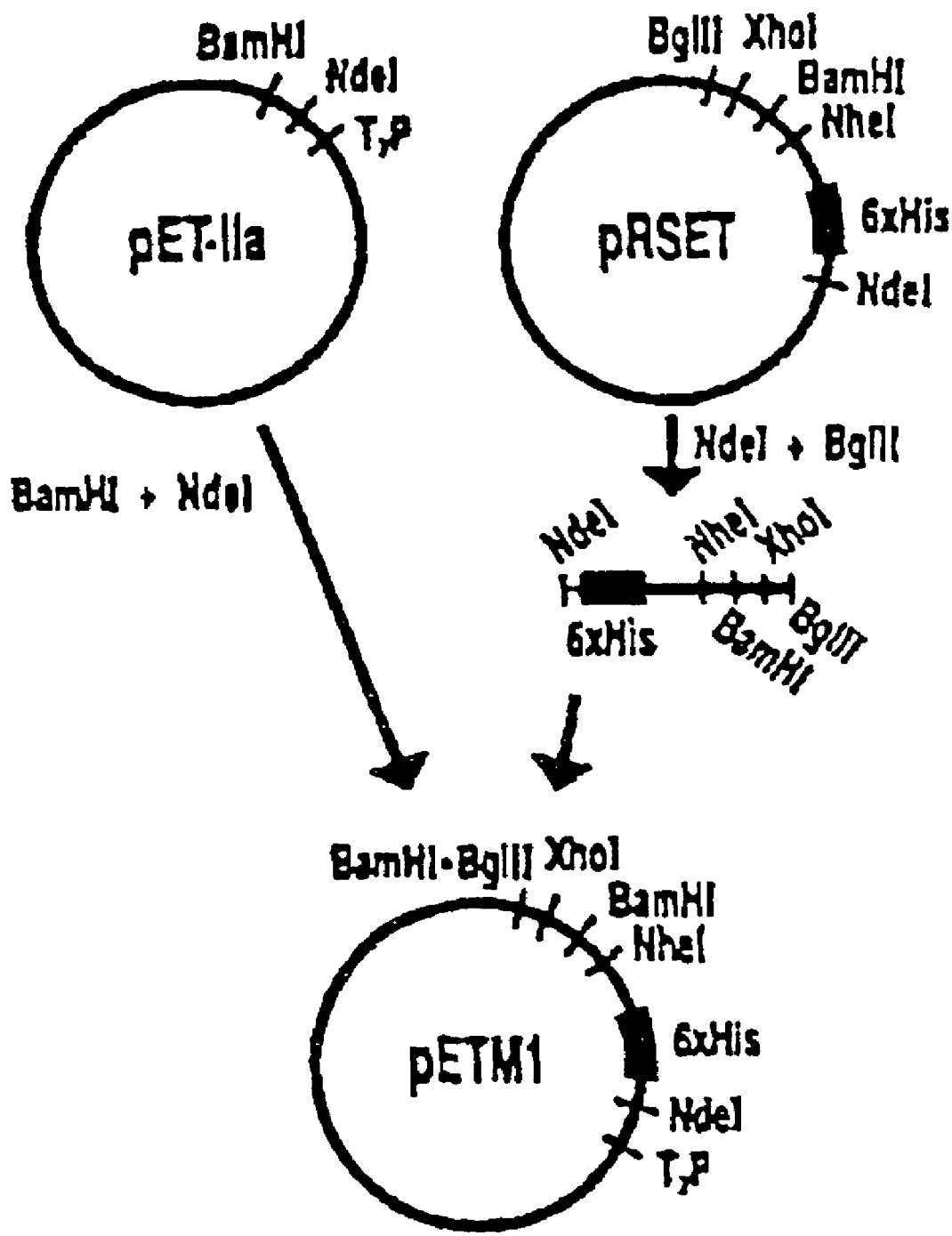
FIG. 8 is a graphical representation of the construction scheme for the vector pETM1 from a commercially available vector.

The coding region of mouse OB cDNA (65–619, Gen-Bank™ Accession No. U18812) was cloned by RT-PCR of total RNA from C57BL/6 white adipose tissue. The coding region was subcloned in expression vector, pETM1 (Feng, L., et al., *J. Biol. Chem.* 269: 2342–2348, 1994), to express a His-tagged recombinant mouse OB protein. The construction of pETM1 from the commercially available vector pET-11a (Novagen, Madison, Wis.) is illustrated on FIG. 8.

After the expression of OB protein is induced, the bacteria were harvested and the inclusion bodies were extracted with a buffer containing 6M urea. The extract was loaded on a Ni-NTA affinity column (Qiagen, Chatsworth, Calif.) and the purification procedure was carried out as previously described (Feng, et al. (1994)). The protein was refolded on the column by adding refolding buffer containing 5 mM $CaCl_2$/20 mM Tris/0.2 NaCl with an urea gradient of 4 M–0.5 M at a rate of about 0.5 ml/minute. After refolding, the protein was eluted with 80 mM imidazole/5 mM $CaCl_2$/20 mM Tris/0.2 NaCl/0.5 mM urea and then dialyzed against phosphate-buffered saline (PBS). Polyclonal antibodies was raised by immunizing a rabbit with the recombinant mouse OB and Freund's adjuvant using standard procedures. Antiserum was used in the following examples.

EXAMPLE 3

Effects of Anti-OB Antibodies on Metabolism

Intravenous administration of antibodies directed against OB protein effectively opposes the effects of endogenous OB protein.

Recombinant mouse OB protein was produced in an *E. coli* expression system as described in Example 2, and was used to generate rabbit polyclonal anti-OB antibody. The antibody, when injected intravenously into mice, stimulated food intake, leading to rapid weight gain, and thus was effective in blocking OB protein function. The results are shown in FIG. 9.

Female C57BL/6 mice, 6–8 weeks of age and 15–17 g of weight, were group housed four per cage and adapted to a 12:12 hour light: dark cycle (light from 6:00 to 18:00). Mice were given a daily intravenous injection of 0.2 ml anti-OB antiserum or preimmune rabbit sera ("vehicle") at 10 p.m., after their initial dark phase food intake. Their body weight was measured at 10 a.m. the next day.

Figure 9:
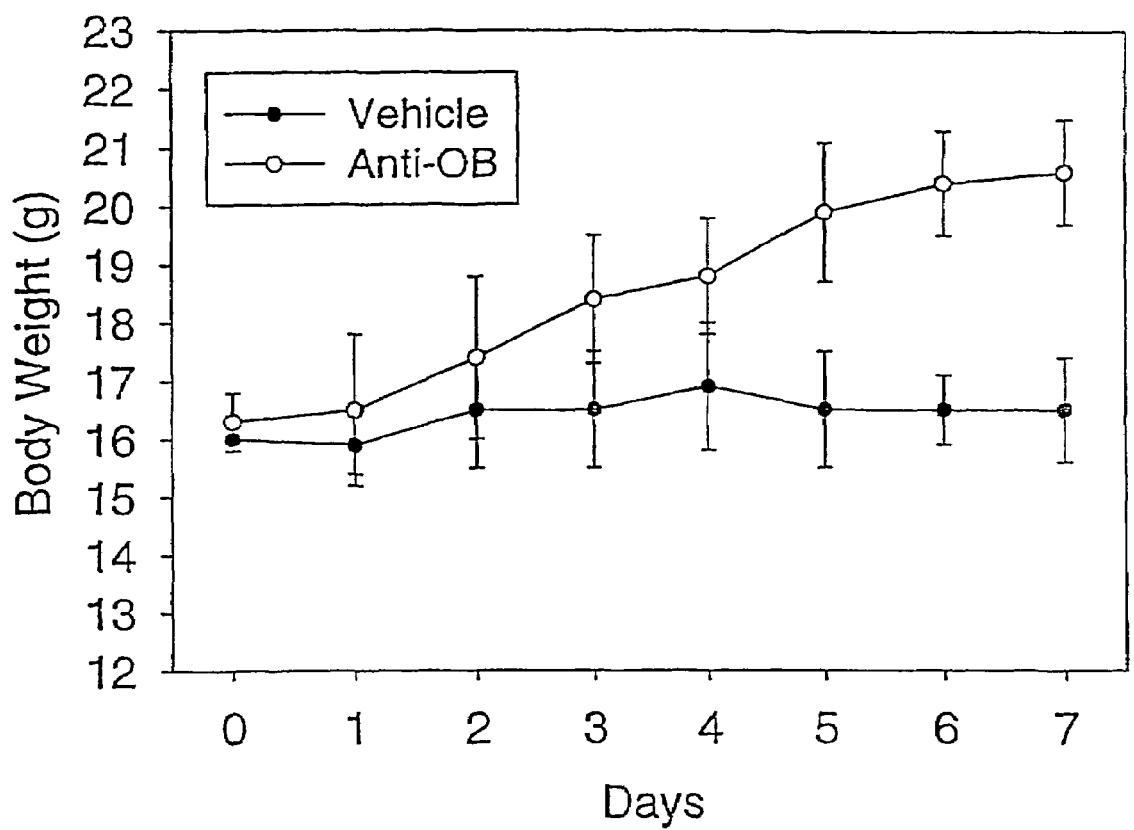
FIG. 9 is a graphical representation of the weight gain induced by anti-OB antiserum injection in C57BL/6 mice which were given daily injections of anti-OB antiserum (antiOB) or preimmune rabbit sera (control), and whose body weight was measured 12 hours later, where data are expressed as mean±standard error of the mean (S.E.M), N=8.

The weight gain induced by anti-OB antiserum is illustrated in FIG. 9. Data are expressed as mean±S.E.M. (N=8). While the weight of the control group remained essentially constant over the week, the anti-OB treated group showed a weight increase at the first weighing, which continued for the entire study period.

EXAMPLE 4

Effects of Anti-OB Antibodies and Recombinant OB-Protein on Response to Endotoxic Shock The fact that the OB-R variants induced in the liver were predominantly short forms raised the question of functional relevance of the hepatic OB-R expression. OB-Rb is the main form expressed in the hypothalamus, while the choroid plexus expresses only OB-Ra. That the mutation in db/db mice affects OB-Rb, but not OB-Ra, suggests that OB-Rb is crucial for regulating food intake and OB-Ra may act as an OB protein transporter. Accordingly, the prominent expression of OB-R in the liver could initiate intracellular signal transduction or, alternatively, mediate the clearance of OB protein. We found that administration of neutralizing anti-OB antibody (Ab) or OB protein to LPS-treated mice distinguished between the two alternatives.

Male C57BL/6 mice, 5–8 weeks of age and 17–21 g of body weight, were used for this study. For antisera treatment, mice were given an i.v. injection of 200 μl rabbit antisera. LPS at a dose of 6 μg per gram of body weight was then co-injected with a second dose of anti-OB antibody to the pretreated mice. LPS was dissolved in antisera at a concentration of 0.6 mg/ml and was injected intravenously 4 hours after the initial antisera treatment. Food was retrieved from mouse cages during the 4-hour pretreatment period to prevent any food intake differences resulting from anti-OB antiserum-induced hyperphagia, and was added back after LPS injection.

Figure 10:
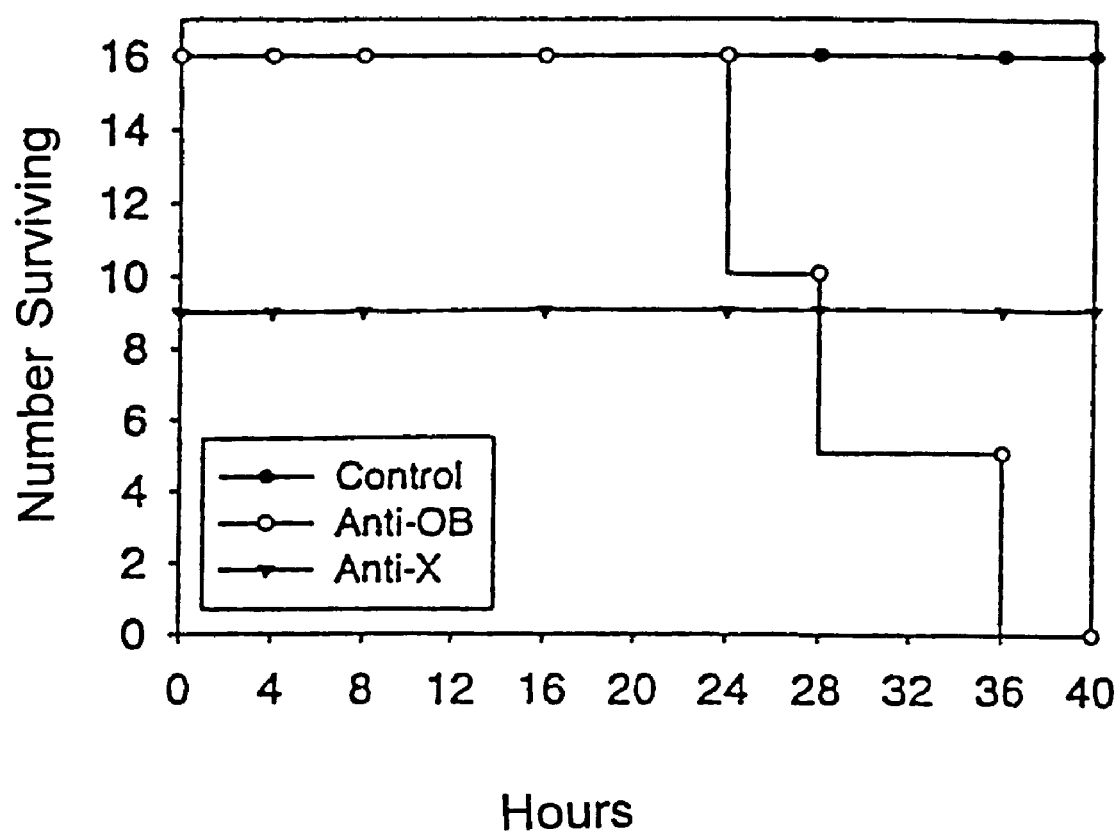
FIG. 10 is a graphical representation of the time course of the survival of mice that had received a LPS injection (6 µg per gram of body weight) after pretreatment with either anti-OB protein antiserum (anti-OB, N=16), preimmune rabbit serum (control, N=16), or one of three other unrelated rabbit antisera (anti-X, N=9: 3 treated with each antiserum)

While this dose of LPS was not lethal to C57BL/6 mice treated with preimmune rabbit serum, all the mice in the anti-OB Ab-treated group died within 40 hours. FIG. 10 illustrates the results from three groups of mice: those pretreated with anti-OB antiserum (anti-OB, N=16), preimmune rabbit sera control, N=16), or three other unrelated rabbit antisera ("Anti-X", N=3 for each antiserum). This LPS sensitizing effect was specific for anti-OB Ab, since mice treated similarly with three other unrelated antibodies ("Anti-X") all survived (FIG. 10).

Figure 11:
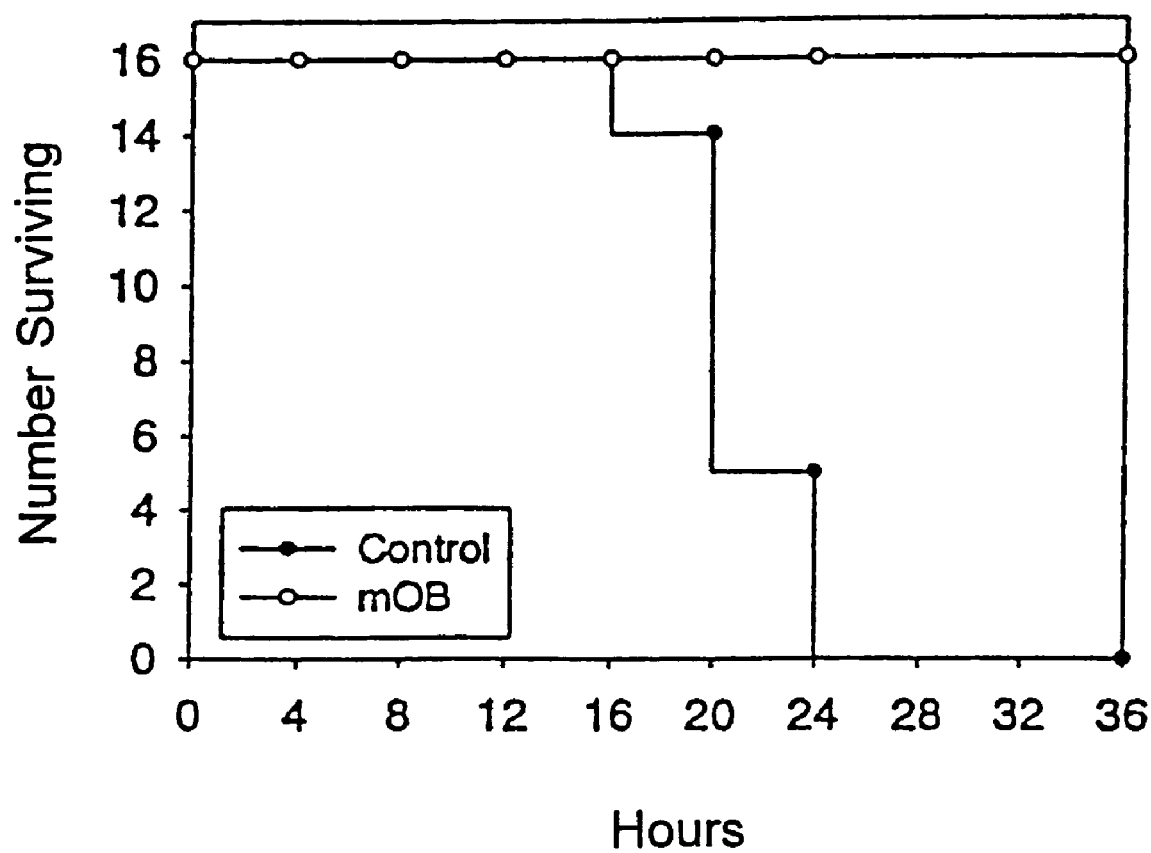
FIG. 11 is a graphical representation of the time course of the survival of mice that were treated with OB protein (mOB, N=16) or vehicle (control, N–16) after a LPS injection (10 µg per gram of body weight)

In comparison, mice treated with OB protein (5 μg per gram of body weight mOB, N=16) were able to survive a higher dose of LPS (10 μg per gram of body weight) that was fatal to the control group of mice receiving the vehicle alone (control, N=16). Mouse OB protein and LPS were prepared in saline at a concentration of 0.5 mg/ml and 1 mg/ml, respectively, and injected intravenously into the mice. A vehicle solution used for OB protein dialysis was injected into control mice. To eliminate any circadian effect, experiments at different days were all started at the same hours. Mice were examined at 4-hour intervals post LPS injection for the first 24 hours, and survival was monitored for 7 days following the LPS injection. The results are shown in FIG. 11. The dose of LPS killed all the mice in the control group within 24 hours. However, in the experimental group, OB protein treatment conferred mice complete resistance to this dose of endotoxin. The OB-treated mice displayed noticeably less severe symptoms of endotoxemia, remaining alert and responsive to touch and other manipulation, and recovering quickly.

The effects of both OB protein and anti-OB antibodies on body temperature and body weight were monitored in the same groups of mice. Core body temperature measurements were made by insertion of a thermistor probe (Yellow Springs Instrument, Yellow Springs, Ohio) into the colon, 1.5 cm beyond the rectum. Body weight measurements were made on a portable digital balance (Ohaus, Florham Park, N.J.).

The mice receiving anti-OB antibodies, which ultimately died, showed lower body temperature (FIG. 12) and less weight loss (FIG. 14) than the corresponding control group than survived. Conversely, the mice receiving OB-protein, and which survived the endotoxic shock, showed higher body temperature (FIG. 13) and more weight loss (FIG. 15) than the corresponding control group which succumbed.

While administration of both OB protein and anti-OB antibodies had significant effects on survival, body weight and body temperature, there was little effect on the expression of iNOS, IL-1α, IL-1β, and TNF-α mRNAs in lung and spleen (FIG. 16). Mice were treated as described in above (FIGS. 10–15).

RNase protection assays were performed as described in Example 1. Each sample was 5 μg total RNA was used for each sample in the RNase assay. Riboprobes were produced as described in Example 1 based on the following cDNA fragments: IL-1α (from base 172 to base 366, Accession No. X01450, SEQ ID NO. 3), IL-1β (from base 500 to base 671, Accession No. M15131, SEQ ID NO. 4), TNF-α (from base 428 to base 557, Accession No. M11731, SEQ ID NO. 5), mouse iNOS (from base 2404 to base 2698, Accession No. M92649, SEQ ID NO. 6), and L32 (from base 33 to base 126, Accession No. X064383, SEQ ID NO. 7).

Relatively little change in the pattern of expression of these markers was observed (FIG. 16), suggesting that these the protective actions of OB proteins are direct and not indirect and mediated by these cytokines.

The foregoing is intended to be illustrative of the present invention, but not limiting. Numerous variations and modifications of the present invention may be effected without departing from the true spirit and scope of the invention.

We claim:

1. A method for conferring resistance to endotoxic shock in an animal in need of resistance to endotoxic shock, comprising administering to said animal a composition having a physiologically effective amount of at least one OB-R agonist ligand.

2. The method of claim 1 wherein the OB-R agonist ligand is recombinant human OB protein.

3. The method of claim 2 wherein the amount of recombinant human OB protein administered is from about 1 microgram per kilogram body weight to about 50 micrograms per kilogram body weight.

4. The method of claim 1 wherein the endotoxic shock occurs in sepsis.

5. The method of claim 1 wherein the endotoxic shock occurs in systemic inflammatory response syndrome.

* * * * *

SEQUENCE LISTING

<160> NUMBER OF SEQ ID NOS: 11

<210> SEQ ID NO 1
<211> LENGTH: 2793
<212> TYPE: DNA
<213> ORGANISM: Mus musculus

<400> SEQUENCE: 1

```
ggatccctgc tccagcagct gcaaggtgca agaagaagaa gatcccaggg aggaaaatgt      60
gctggagacc cctgtgtcgg ttcctgtggc tttggtccta tctgtcttat gttcaagcag     120
tgcctatcca gaaagtccag gatgacacca aaccctcat caagaccatt gtcaccagga     180
tcaatgacat ttcacacacg cagtcggtat ccgccaagca gagggtcact ggcttggact     240
tcattcctgg gcttcacccc attctgagtt tgtccaagat ggaccagact ctggcagtct     300
atcaacaggt cctcaccagc ctgccttccc aaaatgtgct gcagatagcc aatgacctgg     360
agaatctccg agacctcctc catctgctgg ccttctccaa gagctgctcc ctgcctcaga     420
ccagtggcct gcagaagcca gagagcctgg atggcgtcct ggaagcctca ctctactcca     480
cagaggtggt ggctttgagc aggctgcagg gctctctgca ggacattctt caacagttgg     540
atgttagccc tgaatgctga agtttcaaag gccaccaggc tcccaagaat catgtagagg     600
gaagaaacct tggcttccag gggtcttcag gagaagagag ccatgtgcac acatccatca     660
ttcatttctc tccctcctgt agaccaccca tccaaaggca tgactccaca atgcttgact     720
caagttatcc acacaacttc atgagcacaa ggaggggcca gcctgcagag gggactctca     780
cctagttctt cagcaagtag agataagagc catcccatcc cctccatgtc ccacctgctc     840
cgggtacatg ttcctccgtg ggtacacgct tcgctgcggc ccaggagagg tgaggtaggg     900
atgggtagag cctttgggct gtctcagagt ctttgggagc accgtgaagg ctgcatccac     960
acacagctgg aaactcccaa gcagcacacg atggaagcac ttatttattt attctgcatt    1020
ctattttgga tggatctgaa gcaaggcatc agcttttca ggctttgggg gtcagccagg    1080
atgaggaagg ctcctggggt gctgctttca atcctattga tgggtctgcc cgaggcaaac    1140
ctaattttg agtgactgga aggaaggttg ggatcttcca aacaagagtc tatgcaggta    1200
gcgctcaaga ttgacctctg gtgactggtt ttgtttctat tgtgactgac tctatccaaa    1260
cacgtttgca gcggcattgc cgggagcata ggctaggtta ttatcaaaag cagatgaatt    1320
ttgtcaagtg taatatgtat ctatgtgcac ctgagggtag aggatgtgtt agagggaggg    1380
tgaaggatcc ggaagtgttc tctgaattac atatgtgtgg taggcttttc tgaaagggtg    1440
aggcattttc ttacctctgt ggccacatag tgtggctttg tgaaaaggac aaaggagttg    1500
actctttccg gaacatttgg agtgtaccag gcacccttgg aggggctaaa gctacaggcc    1560
ttttgttggc atattgctga gctcagggag tgagggcccc acatttgaga cagtgagccc    1620
caagaaaagg gtccctggtg tagatctcca aggttgtcca gggttgatct cacaatgcgt    1680
```

-continued

```
ttcttaagca ggtagacgtt tgcatgccaa tatgtggttc tcatctgatt ggttcatcca    1740
aagtagaacc ctgtctccca cccattctgt ggggagtttt gttccagtgg aatgagaaa     1800
tcacttagca gatggtcctg agccctgggc cagcactgct gaggaagtgc cagggcccca    1860
ggccaggctg ccagaattgc ccttcgggct ggaggatgaa caaaggggct tgggtttttc    1920
catcacccct gcaccctatg tcaccatcaa actgggggc agatcagtga gaggacactt    1980
gatggaaagc aatacacttt aagactgagc acagtttcgt gctcagctct gtctggtgct    2040
gtgagctaga gaagctcacc acatacatat aaaaatcaga ggctcatgtc cctgtggtta    2100
gaccctactc gcggcggtgt actccaccac agcagcaccg caccgctgga agtacagtgc    2160
tgtcttcaac aggtgtgaaa gaacctgagc tgagggtgac agtgcccagg gaaccctgc    2220
ttgcagtcta ttgcatttac ataccgcatt tcagggcaca ttagcatcca ctcctatggt    2280
agcacactgt tgacaatagg caagggata ggggttgact atcccttatc caaaatgctt     2340
gggactagaa gagttttgga ttttagagtc ttttcaggca taggtatatt tgagtatata    2400
taaaatgaga tatcttgggg atggggccca agtataaaca tgaagttcat ttatatttca    2460
taataccgta tagacactgc ttgaagtgta gtttataca gtgttttaaa taacgttgta     2520
tgcatgaaag acgttttac agcatgaacc tgtctactca tgccagcact caaaaacctt     2580
ggggttttgg agcagtttgg atcttgggtt ttctgttaag agatggttag cttataccta    2640
aaaccataat ggcaaacagg ctgcaggacc agactggatc ctcagccctg aagtgtgccc    2700
ttccagccag gtcataccct gtggaggtga gcgggatcag gttttgtggt gctaagagag    2760
gagttggagg tagattttgg aggatctgag ggc                                 2793
```

<210> SEQ ID NO 2
<211> LENGTH: 3862
<212> TYPE: DNA
<213> ORGANISM: Mus musculus

<400> SEQUENCE: 2

```
gtcgacccac gcgtccggag gaatcgttct gcaaatccag gtgtacacct ctgaagaaag      60
atgatgtgtc agaaattcta tgtggttttg ttacactggg aatttcttta tgtgatagct     120
gcacttaacc tggcatatcc aatctctccc tggaaattta gttgttttg tggaccaccg      180
aacacaaccg atgactcctt tctctcacct gctggagccc caaacaatgc ctcggctttg     240
aagggggctt ctgaagcaat tgttgaagct aaatttaatt caagtggtat ctacgttcct     300
gagttatcca aaacagtctt ccactgttgc tttgggaatg agcaaggtca aaactgctct     360
gcactcacag acaacactga agggaagaca ctggcttcag tagtgaaggc ttcagttttt     420
cgccagctag gtgtaaactg ggacatagag tgctggatga aggggactt gacattattc      480
atctgtcata tggagccatt acctaagaac cccttcaaga attatgactc taaggtccat     540
ctttatatg atctgcctga agtcatagat gattcgcctc tgcccccact gaaagacagc     600
tttcagactg tccaatgcaa ctgcagtctt cggggatgtg aatgtcatgt gccggtaccc     660
agagccaaac tcaactacgc tcttctgatg tatttggaaa tcacatctgc cggtgtgagt     720
tttcagtcac ctctgatgtc actgcagccc atgcttgttg tgaaacccga tccacccta     780
ggtttgcata tggaagtcac agatgatggt aatttaaaga tttcttggga cagccaaaca    840
atggcaccat ttccgcttca atatcaggtg aaatatttag agaattctac aattgtaaga    900
gaggctgctg aaattgtctc agctacatct ctgctggtag acagtgtgct tcctggatct    960
```

-continued

```
tcatatgagg tccaggtgag gagcaagaga ctggatggtt caggagtctg gagtgactgg    1020
agttcacctc aagtctttac cacacaagat gttgtgtatt ttccacccaa aattctgact    1080
agtgttggat cgaatgcttc ttttcattgc atctacaaaa acgaaaacca gattatctcc    1140
tcaaaacaga tagtttggtg gaggaatcta gctgagaaaa tccctgagat acagtacagc    1200
attgtgagtg accgagttag caaagttacc ttctccaacc tgaaagccac cagacctcga    1260
gggaagttta cctatgacgc agtgtactgc tgcaatgagc aggcgtgcca tcaccgctat    1320
gctgaattat acgtgatcga tgtcaatatc aatatatcat gtgaaactga cgggtactta    1380
actaaaatga cttgcagatg gtcacccagc acaatccaat cactagtggg aagcactgtg    1440
cagctgaggt atcacaggcg cagcctgtat tgtcctgata gtccatctat tcatcctacg    1500
tctgagccca aaaactgcgt cttacagaga cggcttttt atgaatgtgt tttcagcca    1560
atctttctat tatctggcta tacaatgtgg atcaggatca accattcttt aggttcactt    1620
gactcgccac caacgtgtgt ccttcctgac tccgtagtaa aaccactacc tccatctaac    1680
gtaaaagcag agattactgt aaacactgga ttattgaaag tatcttggga aaagccagtc    1740
tttccggaga ataaccttca attccagatt cgatatggct taagtggaaa agaaatacaa    1800
tggaagacac atgaggtatt cgatgcaaag tcaaagtctg ccagcctgct ggtgtcagac    1860
ctctgtgcag tctatgtggt ccaggttcgc tgccggcggt tggatggact aggatattgg    1920
agtaattgga gcagtccagc ctatacgctt gtcatggatg taaaagttcc tatgagaggg    1980
cctgaatttt ggagaaaaat ggatgggac gttactaaaa aggagagaaa tgtcaccttg    2040
cttttggaagc ccctgacgaa aaatgactca ctgtgtagtg tgaggaggta cgtggtgaag    2100
catcgtactg cccacaatgg gacgtggtca gaagatgtgg gaaatcggac caatctcact    2160
ttcctgtgga cagaaccagc gcacactgtt acagttctgg ctgtcaattc cctcggcgct    2220
tcccttgtga attttaacct taccttctca tggcccatga gtaaagtgag tgctgtggag    2280
tcactcagtg cttatcccct gagcagcagc tgtgtcatcc tttcctggac actgtcacct    2340
gatgattata gtctgttata tctggttatt gaatggaaga tccttaatga agatgatgga    2400
atgaagtggc ttagaattcc ctcgaatgtt aaaaagtttt atatccacga taatttatt    2460
cccatcgaga aatatcagtt tagtctttac ccagtattta tggaaggagt tggaaaacca    2520
aagataatta atggtttcac caaagatgct atcgacaagc agcagaatga cgcagggctg    2580
tatgtcattg tacccataat tatttcctct tgtgtcctac tgctcggaac actgttaatt    2640
tcacaccaga gaatgaaaaa gttgttttgg acgatgttc caaaccccaa gaattgttcc    2700
tgggcacaag gactgaattt ccaaaagcct gaaacatttg agcatctttt taccaagcat    2760
gcagaatcag tgatatttgg tcctcttctt ctggagcctg aacccatttc agaagaaatc    2820
agtgtcgata cagcttggaa aaataaagat gagatggtcc cagcagctat ggtctcccctt    2880
cttttgacca caccagaccc tgaaagcagt tctatttgta ttagtgacca gtgtaacagt    2940
gctaacttct ctgggtctca gagcacccag gtaacctgtg aggatgagtg tcagagacaa    3000
ccctcagtta aatatgcaac tctggtcagc aacgataaac tagtggaaac tgatgaagag    3060
caagggttta tccatagtcc tgtcagcaac tgcatctcca gtaatcattc cccactgagg    3120
cagtctttct ctagcagctc ctgggagaca gaggcccaga cattttttcct tttatcagac    3180
cagcaaccca ccatgatttt accacaactt tcattctcgg ggttggatga gcttttggaa    3240
ctggagggaa gttttcctga gaaaaatcac agggagaagt ctgtctgtta tctaggagtc    3300
acctccgtca acagaagaga gagtggtgtg cttttgactg gtgaggcagg aatcctgtgc    3360
```

-continued

```
acattcccag cccagtgtct gttcagtgac atcaggatcc tccaggagag atgctcacac      3420
tttgtagaaa ataatttgag tttagggacc tctggtgaga actttgtacc ttacatgccc      3480
caatttcaaa cctgttccac gcacagtcac aagataatgg agaataagat gtgtgactta      3540
actgtgtaat ctcatccaag aagcctcaag gttccattcc agtagagcct gtcatgtata      3600
atgtgttctt ttattgttgt ggatgtggga gacaagtgtc agaatctagt gtgaaaatga      3660
ttgtttccaa actaagtgtg tctatttcct ctcagtaata caatgaaaca tatgaggaag      3720
ccctcattaa tctagtaatg tagatggact cttactgaat atattcccaa gatacttggg      3780
gaagtctccc taattctagc taaaaataaa cccaggaata gaactactaa acactgaatc      3840
tggaaaaaaa aaaaaaaaaa ag                                               3862

<210> SEQ ID NO 3
<211> LENGTH: 1974
<212> TYPE: DNA
<213> ORGANISM: Mus musculus

<400> SEQUENCE: 3
aagtctccag ggcagagagg gagtcaactc attggcgctt gagtcggcaa agaaatcaag       60
atggccaaag ttcctgactt gttttgaagac ctaaagaact gttacagtga aaacgaagac     120
tacagttctg ccattgacca tctctctctg aatcagaaat ccttctatga tgcaagctat     180
ggctcacttc atgagacttg cacagatcag tttgtatctc tgagaaccct gaaacgtca      240 aagatgtcca acttcacctt caaggagagc cgggtgacag tatcagcaac gtcaagcaac     300 ggaagattc tgaagaagag acggctgagt ttcagtgaga ccttcactga agatgacctg      360
cagtccataa cccatgatct ggaagagacc atccaaccca gatcagcacc ttacacctac     420
cagagtgatt tgagatacaa actgatgaag ctcgtcaggc agaagtttgt catgaatgat     480
tccctcaacc aaactatata tcaggatgtg acaaacact atctcagcac cacttggtta     540
aatgacctgc aacaggaagt aaaatttgac atgtatgcct actcgtcggg aggagacgac     600
tctaaatatc ctgttactct aaaaatctca gattcacaac tgttcgtgag cgctcaagga     660
gaagaccagc ccgtgttgct gaaggagttg ccagaaacac caaaactcat acaggtagt     720 gagaccgacc tcattttctt ctggaaaagt atcaactcta agaactactt cacatcagct     780
gcttatccag agctgtttat tgccaccaaa gaacaaagtc gggtgcacct ggcacgggga     840 ctgcccctcta tgacagactt ccagatatca taaaagcagc cttatttcgg gagtctattc    900
acttgggaag tgctgacagt ctgtatgtac catgtacagg aaccttcctc accctgagtc     960
acttgcacag catgtgctga gtctctgtaa ttctaaatga atgtttaccc tctttgtaag    1020
agaagagcaa accctagtgg agccacccg acatatgata ctatctgtta ttttaaagag    1080 tacccctatag tttgctcagt actaatcatt ttaattacta ttctgcatgg cattcttagg   1140
aggatcaaaa agactctaca catattacag atgggttaac aaagggataa acaactgaa    1200 aagcacactc aatgcatttg gaatataaat tcacagacca atctcactgt gcaccttcgg    1260
cttcaaaatg ccagttgagt aggataaagg tataagaact taatgctgtc attttcaaaa    1320
ggaaggggac aatagctaca tcttttcctac ctcagtgggt tttactccag tgagatcatt   1380
tggatgaaat cctcctgtaa cagacctcaa gaaggagaca gactgttgaa tgttatttttt   1440 aagttatttt atatatgtat ttataaatat atttatgata attatattat ttatggaaca   1500
tccttaaatc ctctgagctt gacaggcatc ctcacagcag gattttctag gtggtcagtt   1560
```

```
agatatagtt tcctctagag caccatgcta cagactttac acttttttcca cagccacgaa    1620 gctctctgta cattcctgta cttgggagcc ctttcatcat gatcttaatc tgtactgttt    1680
actttgttca tctaaaatga taattgagtc agtcttttc cctcccatcc ttaaagctgt    1740
ctgggtattc ttacatcatt cagtctcacc tgtaactaac accaaccatc taaagatgga    1800
aagagcttaa ctgtgacaac cacatcactg ttacctgaag tttctttttct agaatgtaat    1860 cagtgttttcc cctggattcc aatttttttt tcaaaccaca gtatcatgta actatcaaca    1920
ataacaatca actcattatt attaatcata attaaataaa acaagtttga gctg          1974

<210> SEQ ID NO 4
<211> LENGTH: 1339
<212> TYPE: DNA
<213> ORGANISM: Mus musculus

<400> SEQUENCE: 4
tgcagggttc gaggcctaat aggctcatct gggatcctct ccagccaagc ttccttgtgc      60
aagtgtctga agcagctatg gcaactgttc ctgaactcaa ctgtgaaatg ccaccttttg    120
acagtgatga gaatgacctg ttctttgaag ttgacggacc ccaaaagatg aagggctgct    180
tccaaacctt tgacctgggc tgtccagatg agagcatcca gcttcaaatc tcacagcagc    240
acatcaacaa gagcttcagg caggcagtat cactcattgt ggctgtggag aagctgtggc    300
agctacctgt gtcttttccg tggaccttcc aggatgagga catgagcacc ttctttttcct    360 tcatctttga agaagagccc atcctctgtg actcatggga tgatgatgat aacctgctgg    420
tgtgtgacgt tcccattaga cagctgcact acaggctccg agatgaacaa caaaaaagcc    480
tcgtgctgtc ggacccatat gagctgaaag ctctccacct caatgacag aatatcaacc    540 aacaagtgat attctccatg agctttgtac aaggagaacc aagcaacgac aaaataccctg    600 tggccttggg cctcaaagga aagaatctat acctgtcctg tgtaatgaaa gacggcacac    660
ccaccctgca gctggagagt gtggatccca agcaataccc aaagaagaag atggaaaagc    720 ggttttgtctt caacaagata gaagtcaaga gcaaagtgga gttgagtct gcagagttcc    780 ccaactggta catcagcacc tcacaagcag agcacaagcc tgtcttcctg ggaaacaaca    840
gtggtcagga cataattgac ttcaccatgg aatctgtgtc ttcctaaagt atgggctgga    900
ctgtttctaa tgccttcccc agggcatgtg aaggagctcc cttgtcatga atgagcagac    960
agctcaatct ctaggacact ccttagtcct cggccaagac aggtcgctca gggtcacaag   1020
aaaccatggc acattctgtt caaagagagc ctgtgtttcc tccttgcctc tgatgggcaa   1080
ccacttacct atttatttat gtatttattg attggttgat ctatttaagt tgattcaagg   1140
ggacattagg cagcactctc tagaacagaa cctagctgtc aacgtgtggg ggatgaattg   1200
gtcatagcct tgcacttgag gtctttcatt gaagctgaga ataaataggt tcctataata   1260
tggatgagaa ttttttatgaa tgaagcatta gcacattgct ttgatgagta tgaaataaat   1320
ttcattaaac aaacaaaca                                                 1339

<210> SEQ ID NO 5
<211> LENGTH: 1629
<212> TYPE: DNA
<213> ORGANISM: Mus musculus

<400> SEQUENCE: 5
gctgagggac tagccaggag ggagaacaga aactccagaa catcctggaa atagctccca      60
gaaaagcaag cagccaacca ggcaggttct gtcccttttca ctcactggcc caaggcgcca    120
```

```
catctccctc cagaaaagac accatgagca cagaaagcat gatccgcgac gtggaactgg    180
cagaagaggc actcccccaa aagatggggg gcttccagaa ctccaggcgg tgcctatgtc    240
tcagcctctt ctcattcctg cttgtggcag gggccaccac gctcttctgt ctactgaact    300
tcggggtgat cggtccccaa agggatgaga agttcccaaa tggcctccct ctcatcagtt    360
ctatggccca gaccctcaca ctcagatcat cttctcaaaa ttcgagtgac aagcctgtag    420
cccacgtcgt agcaaaccac caagtggagg agcagctgga gtggctgagc cagcgcgcca    480
acgccctcct ggccaacggc atggatctca agacaaccca actagtggtg ccagccgatg    540
ggttgtacct tgtctactcc caggttctct tcaagggaca aggctgcccc gactacgtgc    600
tcctcaccca caccgtcagc cgatttgcta tctcatacca ggagaaagtc aacctcctct    660
ctgccgtcaa gagcccctgc cccaaggaca cccctgaggg ggctgagctc aaaccctggt    720
atgagcccat atacctggga ggagtcttcc agctggagaa gggggaccaa ctcagcgctg    780
aggtcaatct gcccaagtac ttagactttg cggagtccgg gcaggtctac tttggagtca    840
ttgctctgtg aagggaatgg gtgttcatcc attctctacc cagcccccac tctgaccccc    900
ttactctgac ccctttattg tctactcctc agagccccca gtctgtgtcc ttctaactta    960
gaaaggggat tatggctcag agtccaactc tgtgctcaga gctttcaaca actactcaga   1020
aacacaagat gctgggacag tgacctggac tgtgggcctc tcatgcacca ccacccacgg   1080
aatcgagaaa gagctatcaa tctggaattc actggagcct cgaatgtcca ttcctgagtt   1140
ctgcaaaggg agagtggtca ggttgcctct gtctcagaat gaggctggat aagatctcag   1200
gccttcctac cttcagacct ttccagactc ttccctgagg tgcaatgcac agccttcctc   1260
acagagccag ccccctcta tttatatttg cacttattat ttattattta tttattattt   1320
atttatttgc ttatgaatgt atttatttgg aaggccgggg tgtcctggag acccagtgt   1380
gggaagctgt cttcagacag acatgttttc tgtgaaaacg gagctgagct gtccccacct   1440
ggcctctcta ccttgttgcc tcctcttttg cttatgttta aaacaaaata tttatctaac   1500
ccaattgtct taataacgct gatttggtga ccaggctgtc gctacatcac tgaacctctg   1560
ctccccacgg gagccgtgac tgtaattgcc ctacgggtca ttgagagaaa taaagatcgc   1620
ttggaaaag                                                          1629

<210> SEQ ID NO 6
<211> LENGTH: 4110
<212> TYPE: DNA
<213> ORGANISM: Mus musculus

<400> SEQUENCE: 6
gagactctgg ccccacggga cacagtgtca ctggtttgaa acttctcagc caccttggtg     60
aagggactga gctgttagag acacttctga ggctcctcac gcttgggtct tgttcactcc    120
acggagtagc ctagtcaact gcaagagaac ggagaacgtt ggatttggag cagaagtgca    180
aagtctcaga catggcttgc ccctggaagt ttctcttcaa agtcaaatcc taccaaagtg    240
acctgaaaga ggaaaaggac attaacaaca acgtgaagaa aaccccttgt gctgttctca    300
gcccaacaat acaagatgac cctaagagtc accaaaatgg ctccccgcag ctcctcactg    360
ggacagcaca gaatgttcca gaatccctgg acaagctgca tgtgacatcg acccgtccac    420
agtatgtgag gatcaaaaac tggggcagtg gagagatttt gcatgacact cttcaccaca    480
aggccacatc ggatttcact tgcaagtcca agtcttgctt ggggtccatc atgaacccca    540
```

| | |
|---|---|
| agagtttgac cagaggaccc agagacaagc ctacccctct ggaggagctc ctgcctcatg | 600 |
| ccattgagtt catcaaccag tattatggct cctttaaaga ggcaaaaata gaggaacatc | 660 |
| tggccaggct ggaagctgta acaaaggaaa tagaaacaac aggaacctac cagctcactc | 720 |
| tggatgagct catctttgcc accaagatgg cctggaggaa tgtccctcgc tgcatcggca | 780 |
| ggatccagtg gtccaacctg caggtctttg acgctcggaa ctgtagcaca gcacaggaaa | 840 |
| tgtttcagca catctgcaga cacatacttt atgccaccaa caatggcaac atcaggtcgg | 900 |
| ccatcactgt gttcccccag cggagtgacg gcaaacatga cttcaggctc tggaattcac | 960 |
| agctcatccg gtacgctggc taccagatgc ccgatgcac catcagaggg gatgctgcca | 1020 |
| ccttggagtt cacccagttg tgcatcgacc taggctggaa gccccgctat ggccgctttg | 1080 |
| atgtgctgcc tctggtcttg caagctgatg gtcaagatcc agaggtcttt gaaatccctc | 1140 |
| ctgatcttgt gttggaggtg accatggagc atcccaagta cgagtggttc aggagctcg | 1200 |
| ggttgaagtg gtatgcactg cctgccgtgg ccaacatgct actggaggtg ggtggcctcg | 1260 |
| aattcccagc ctgccccttc aatggttggt acatgggcac cgagattgga gttcgagact | 1320 |
| tctgtgacac acagcgctac aacatcctgg aggaagtggg ccgaaggatg ggcctggaga | 1380 |
| cccacacact ggcctccctc tggaaagacc gggctgtcac ggagatcaat gtggctgtgc | 1440 |
| tccatagttt ccagaagcag aatgtgacca tcatggacca ccacacagcc tcagagtcct | 1500 |
| tcatgaagca catgcagaat gagtaccggg cccgtggagg ctgcccggca gactggattt | 1560 |
| ggctggtccc tccagtgtct gggagcatca cccctgtgtt ccaccaggag atgttgaact | 1620 |
| atgtcctatc tccattctac tactaccaga tcgagccctg gaagacccac atctggcaga | 1680 |
| atgagaagct gaggcccagg aggagagaga tccgatttag agtcttggtg aaagtggtgt | 1740 |
| tctttgcttc catgctaatg cgaaaggtca tggcttcacg ggtcagagcc acagtcctct | 1800 |
| ttgctactga gacagggaag tctgaagcac tagccaggga cctggccacc ttgttcagct | 1860 |
| acgccttcaa caccaaggtt gtctgcatgg accagtataa ggcaagcacc ttggaagagg | 1920 |
| agcaactact gctggtggtg acaagcacat ttgggaatgg agactgtccc agcaatgggc | 1980 |
| agactctgaa gaaatctctg ttcatgctta gagaactcaa ccacaccttc aggtatgctg | 2040 |
| tgtttggcct tggctccagc atgtaccctc agttctgcgc cttttgctcat gacatcgacc | 2100 |
| agaagctgtc ccacctggga gcctctcagc ttgccccaac aggagaaggg gacgaactca | 2160 |
| gtgggcagga ggatgccttc cgcagctggg ctgtacaaac cttccgggca gcctgtgaga | 2220 |
| cctttgatgt ccgaagcaaa catcacattc agatcccgaa acgcttcact tccaatgcaa | 2280 |
| catgggagcc acagcaatat aggctcatcc agagcccgga gcctttagac ctcaacagag | 2340 |
| ccctcagcag catccatgca aagaacgtgt ttaccatgag gctgaaatcc cagcagaatc | 2400 |
| tgcagagtga aaagtccagc cgcaccaccc tcctcgttca gctcaccttc gagggcagcc | 2460 |
| gagggcccag ctacctgcct ggggaacacc tggggatctt cccaggcaac cagaccgccc | 2520 |
| tggtgcaggg aatcttggag cgagttgtgg attgtcctac accacaccaa actgtgtgcc | 2580 |
| tggaggttct ggatgagagc ggcagctact gggtcaaaga caagaggctg ccccctgct | 2640 |
| cactcagcca gcccctcacc tacttcctgg acattacgac ccctcccacc cagctgcagc | 2700 |
| tccacaagct ggctcgcttt ggcacggacg agacggatag gcagagattg gaggccttgt | 2760 |
| gtcagccctc agagtacaat gactggaagt tcagcaacaa ccccacgttc ctggaggtgc | 2820 |
| ttgaagagtt cccttccttg catgtgcccg ctgccttcct gctgtcgcag ctccctatct | 2880 |
| tgaagccccg ctactactcc atcagctcct cccaggacca cacccctcg gaggttcacc | 2940 |

-continued

```
tcactgtggc cgtggtcacc taccgcaccc gagatggtca gggtcccctg caccatggtg    3000
tctgcagcac ttggatcagg aacctgaagc cccaggaccc agtgccctgc tttgtgcgaa    3060
gtgtcagtgg cttccagctc cctgaggacc cctcccagcc ttgcatcctc attgggcctg    3120
gtacgggcat tgctcccttc cgaagtttct ggcagcagcg gctccatgac tcccagcaca    3180
aagggctcaa aggaggccgc atgagcttgg tgtttgggtg ccggcacccg gaggaggacc    3240
acctctatca ggaagaaatg caggagatgg tccgcaagag agtgctgttc caggtgcaca    3300
caggctactc ccggctgccc ggcaaaccca aggtctacgt tcaggacatc ctgcaaaagc    3360
agctggccaa tgaggtactc agcgttctcc acggggagca gggccacctc tacatttgcg    3420
gagatgtgcg catggctcgg gatgtggcta ccacattgaa gaagctggtg ccaccaagc     3480 tgaacttgag cgaggagcag gtggaagact atttcttcca gctcaagagc cagaaacgtt    3540
atcatgaaga tatcttcggt gcagtctttt cctatgggc aaaaaagggc agcgccttgg     3600
aggagcccaa agccacgagg ctctgacagc ccagagttcc agcttctggc actgagtaaa    3660
gataatggtg aggggcttgg ggagacagcg aaatgcaatc ccccccaagc ccctcatgtc    3720
attcccccct cctccaccct accaagtagt attgtattat tgtggactac taaatctctc    3780
tcctctcctc cctcccctct ctccctttcc tccttcttc tccactcccc agctccctcc     3840
ttctccttct cctcctttgc ctctcactct tccttggagc tgagagcaga gaaaaactca    3900
acctcctgac tgaagcactt tgggtgacca ccaggaggca ccatgccgcc gctctaatac    3960
ttagctgcac tatgtacaga tatttatact tcatatttaa gaaaacagat acttttgtct    4020
actcccaatg atggcttggg cctttcctgt ataattcctt gatgaaaaat atttatataa    4080
aatacatttt attttaatca aaaaaaaaaa                                     4110
```

<210> SEQ ID NO 7
<211> LENGTH: 465
<212> TYPE: DNA
<213> ORGANISM: Rattus norvegicus

<400> SEQUENCE: 7

```
ggcatcatgg ctgcccttcg gcctctggtg aagcccaaga tcgtcaaaaa gaggaccaag     60
aagttcatca ggcaccagtc ggaccgatat gtgaaaatta gcgaaactg gcggaaaccc     120 agaggcatcg acaacagggt gcggagaaga ttcaagggcc agatcctgat gcccaacatt    180
ggttacggga gtaacaagaa aaccaagcac atgctgccta cgggcttccg gaagtttctg    240
gtccacaatg tcaaggagct ggaagtgctg ctgatgtgca acaaatctta ctgtgctgag    300
attgctcaca atgtgtcctc taagaaccga aaagccatcg tagaaagagc agcacagctg    360
gccatcagag tcaccaatcc caacgccagg ctacgcagcg aagagaatga atagatggct    420
tgtgtgcctg ttttgtgttc aaataaaacc acaaaaactg ccaaa                    465
```

<210> SEQ ID NO 8
<211> LENGTH: 21
<212> TYPE: DNA
<213> ORGANISM: Mus musculus

<400> SEQUENCE: 8

```
gctatcgaca agcagcagaa t                                               21
```

<210> SEQ ID NO 9
<211> LENGTH: 22
<212> TYPE: DNA

```
<213> ORGANISM: Mus musculus

<400> SEQUENCE: 9
tgaacacaac aacataaagc cc                                                    22

<210> SEQ ID NO 10
<211> LENGTH: 26
<212> TYPE: DNA
<213> ORGANISM: Mus musculus

<400> SEQUENCE: 10
tgttatatct ggttattatt gaatgg                                                26

<210> SEQ ID NO 11
<211> LENGTH: 27
<212> TYPE: DNA
<213> ORGANISM: Mus musculus

<400> SEQUENCE: 11
cattaaatga tttattatca gaattgc                                               27
```